United States Patent
Jaeger et al.

(10) Patent No.: US 11,453,897 B2
(45) Date of Patent: Sep. 27, 2022

(54) METHOD FOR PRODUCING AMINOBENZOIC ACID OR AN AMINOBENZOIC ACID DERIVATIVE PRODUCT

(71) Applicant: Covestro Intellectual Property GmbH & Co. KG, Leverkusen (DE)

(72) Inventors: Gernot Jaeger, Cologne (DE); Guenter Olf, Zülpich (DE); Franz Beggel, Cologne (DE); Wolf Kloeckner, Cologne (DE); Simon Klaff, Düsseldorf (DE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 0 days.

(21) Appl. No.: 15/733,917

(22) PCT Filed: Jun. 5, 2019

(86) PCT No.: PCT/EP2019/064627
§ 371 (c)(1),
(2) Date: Dec. 1, 2020

(87) PCT Pub. No.: WO2019/234092
PCT Pub. Date: Dec. 12, 2019

(65) Prior Publication Data
US 2021/0222215 A1    Jul. 22, 2021

(30) Foreign Application Priority Data

Jun. 7, 2018 (EP) .................................... 18176433

(51) Int. Cl.
| C12P 13/00 | (2006.01) |
| C12N 1/20  | (2006.01) |
| C12N 1/32  | (2006.01) |
| C12N 9/10  | (2006.01) |
| C12N 15/77 | (2006.01) |

(52) U.S. Cl.
CPC .......... *C12P 13/001* (2013.01); *C12N 9/1077* (2013.01); *C12N 15/77* (2013.01); *C12P 13/00* (2013.01); *C12Y 204/02018* (2013.01)

(58) Field of Classification Search
CPC ...... C12P 13/001; C12P 13/04; C07C 209/68; C07C 211/46
USPC ...................... 435/136, 128, 252.2
See application file for complete search history.

(56) References Cited

U.S. PATENT DOCUMENTS

| 4,851,570 | A  | 7/1989  | Zaby et al.    |
| 5,053,539 | A  | 10/1991 | Yano et al.    |
| 5,286,760 | A  | 2/1994  | Bolton et al.  |
| 6,433,219 | B1 | 8/2002  | Strofer et al. |
| 7,253,321 | B2 | 8/2007  | Hagen et al.   |
| 7,547,801 | B2 | 6/2009  | Pohl et al.    |
| 7,692,042 | B2 | 4/2010  | Dugal et al.   |
| 8,079,752 | B2 | 12/2011 | Rausch et al.  |
| 8,097,751 | B2 | 1/2012  | Koch et al.    |
| 8,455,691 | B2 | 6/2013  | Sommer et al.  |
| 2007/0238901 | A1 | 10/2007 | Dugal et al. |
| 2010/0094051 | A1 | 4/2010  | Nishi et al. |
| 2010/0324336 | A1 | 12/2010 | Sommer et al. |

FOREIGN PATENT DOCUMENTS

| DE | 10149869 A1      | 4/2003 |
| EP | 2562263 A1       | 2/2013 |
| WO | WO 2015/124687   | 8/2015 |
| WO | WO 2015124686 A1 | 8/2015 |
| WO | WO 2017102853 A1 | 6/2017 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Kisselev L., (Structure, 2002, vol. 10: 8-9.*
Qian-Zhu Li et al, "Recovery processes of organic acids from fermentation broths in the biomass-based industry", Journal of Microbiology and Biotechnology, vol. 26, Sep. 25, 2015, pp. 1-8, XP002762999.
Chem. Biochem. Eng. Q. 19 (2) 159-172 (2005).
Chemical Engineering and Processing, 81 (2014) 59-71.
Wiklund, Current Organic Synthesis, 2006, 3, 379-402.
Decker and Frye, Z. Naturforschg. 21 b, 522-526 [1966].
Balderas-Hernandez, V. E. et al., "Metabolic engineering for improving anthranilate synthesis from glucose in *Escherichia coli*", Microb. Cell. Fact. 2009, 8, 19 (doi: 10.118611475-2859-8-19).
Bhavana Guptaa et al., Polymers Advanced Technologies, 2011, 22, 1982-1988.
International Search Report, PCT/EP2019/064627, dated Aug. 7, 2019, Authorized officer: Ruth Boeker.

\* cited by examiner

*Primary Examiner* — Tekchand Saidha
*Assistant Examiner* — Mohammad Y Meah
(74) *Attorney, Agent, or Firm* — Jed C. Benson

(57) ABSTRACT

The invention relates to a method for producing aminobenzoic acid or an aminobenzoic acid derivative using a fermentation process, in which (I) the aminobenzoic acid formed in the fermentation broth obtained by the fermentation is bound in part, or as much as possible based on the solubility equilibrium, as insoluble calcium-aminobenzoate, said insoluble calcium-aminobenzoate is then (II) either isolated as such or in a mixture with the microorganism used in the fermentation and transitioned into a water soluble form, while separating an insoluble calcium salt which is different from the calcium-aminobenzoate, and then (III) by introducing carbon dioxide under pressure into the aqueous solution from the precipitated calcium salt has been released, aminobenzoic acid is precipitated.

19 Claims, 4 Drawing Sheets

METHOD FOR PRODUCING AMINOBENZOIC ACID OR AN AMINOBENZOIC ACID DERIVATIVE PRODUCT

CROSS-REFERENCE TO RELATED APPLICATIONS

This application is a national stage application under 35 U.S.C. § 371 of PCT/EP2019/064627, filed Jun. 5, 2019, which claims the benefit of European Application No. 18176433.3, filed Jun. 7, 2018, each of which is incorporated herein by reference.

FIELD

The present invention relates to a process for preparing aminobenzoic acid or an aminobenzoic acid conversion product using a fermentation process in which
(I) the aminobenzoic acid formed in the fermentation broth obtained by the fermentation is partly, if appropriate as far as possible on account of the solubility equilibrium, bound as insoluble calcium aminobenzoate, and this insoluble calcium aminobenzoate is then
(II) isolated either as such or in a mixture with the microorganisms used in the fermentation and converted to a water-soluble form with separation of an insoluble calcium salt other than calcium aminobenzoate, and then
(III) aminobenzoic acid is precipitated by introducing carbon dioxide under pressure into the aqueous solution freed of the precipitated calcium salt.

BACKGROUND

The preparation of organic acids by fermentation processes has gained particular attention in the recent past. A particular non-trivial factor here is the isolation of the desired product from the fermentation broth obtained in an economic manner. The isolation of organic acids from fermentation broths has already been the subject of scientific studies; see, for example, *J. Microbiol. Biotechnol.* (2016), 26(1), 1-8. What is described there includes the obtaining of organic acids such as lactic acid, citric acid and succinic acid by precipitation as ammonium or calcium salts. What is described by way of example is isolation by precipitation with $Ca(OH)_2$ or $CaCO_3$, followed by filtration and dissolution of the calcium salts filtered off with sulfuric acid. The consumption of calcium salts and the formation of calcium sulfate, which is of low value, are described as drawbacks of this method. Further documents are also concerned with the obtaining of these and other organic acids from fermentative production; see EP 2 562 263 A1 and *Chem. Biochem. Eng. Q.* 19 (2) 159-172 (2005) (lactic acid), US 2010/0094051 A1 (succinic acid) and *Chemical Engineering and Processing*, 81 (2014) 59-71 (glutamic acid).

German patent application DE 101 49 869 A1 relates to a process for isolating salts of organic acids from an aqueous solution, especially from a fermentation discharge, by partial evaporative crystallization and subsequent or simultaneous displacement precipitation of the salt thereof, and for release of the organic acid from the crystallizate, preferably by means of an electromembrane process. In a preferred embodiment, the organic acid is a carboxylic acid, especially polyhydroxycarboxylic acids such as 2-keto-polyhydroxy-C6-carboxylic acids. Also mentioned as possible acids are ketogulonic acids, lactic acid, citric acid, vanillic acid, idonic acid and gulonic acid, with particular emphasis on the ketogulonic acids 2,4-diketo-D-gulonic acid, 2,5-diketo-D-gulonic acid, 2-keto-L-gulonic acid and ascorbic acid.

Among the organic acids obtainable by fermentation, particular emphasis should be given to aminobenzoic acid as an economically important product which is used either as such or as an intermediate in the preparation of other compounds derived from the aminobenzoic acid by further chemical reaction(s) (referred to henceforth as aminobenzoic acid conversion products). For example, aminobenzoic acid is used in the preparation of dyes, odorants or pharmaceuticals (Wiklund, Current Organic Synthesis, 2006, 3, 379-402). An example of an important aminobenzoic acid conversion reaction for preparation of another product is decarboxylation to give aniline, which, for its part, is of importance especially as an intermediate in the preparation of isocyanates.

Aminobenzoic acid has also attracted the interest of scientific studies. For instance, Decker and Frye as early as 1966 studied the properties of the substitution pattern on the chelate-forming properties of aminobenzoic acids (cf. Z. Naturforschg. 21 b, 522-526 [1966]). Chelates of aminobenzoate with Mg(II), Ca(II), Cr(III), Mn(II), Fe(II), Fe(III), Co(II), Ni(II), Cu(II), Cd(II) and Zn(II) were studied.

Fermentative preparation of aminobenzoic acid is described in the literature. Reference is made by way of example to Balderas-Hemandez, V. E. et al., "Metabolic engineering for improving anthranilate synthesis from glucose in *Escherichia coli*", *Microb. Cell. Fact.* 2009, 8, 19 (doi: 10.118611475-2859-8-19). The patent literature also includes publications in this regard; see, for example, the applications WO 2015/124686 A1 and WO 2015/124687 A1 and the literature cited in each. Fermentation processes proceed in an aqueous medium and, in the case of preparation of aminobenzoic acid, afford aqueous product mixtures (fermentation broths) with a content by mass of aminobenzoic acid in the range from 10.0 g/L to 100 g/L.

Of particular significance is the ortho isomer of aminobenzoic acid, anthranilic acid. In the metabolism of bacteria and yeasts, anthranilic acid is formed in the shikimic acid pathway as a natural intermediate in the synthesis of tryptophan. In the biotechnological production of anthranilic acid, the conversion thereof in the metabolic pathway is reduced or suppressed in order to achieve accumulation in the fermentation medium. Such a concept for biological production of anthranilic acid and the subsequent catalytic conversion thereof to aniline is described in the international patent applications WO 2015/124686 A1 and WO 2015/124687 A1 that have already been mentioned. A possible recombinant microorganism described is the use of bacteria from the families of the corynebacteria or pseudomonads. A more recent application (WO 2017/102853 A1) describes the use of yeasts.

If the aim is fermentative production of anthranilic acid in a neutral to alkaline pH range (as described by WO 2015/124686 A1 and WO 2015/124687 A1), the addition of a base is required to neutralize the acid and to prevent too great a reduction in pH in the course of fermentation. Anthranilic acid is present as the anion (aminobenzoate) in a neutral to alkaline pH range. Which cation is present in the fermentation broth depends on the base used for neutralization. In one embodiment of the processes described, after the fermentation, the pH is reduced by adding an acid to a value of or close to pH 3.5 (isoelectric point), i.e. dissolved aminobenzoate is converted back to the acid or the "zwitterion" ($^-OOC-C_6H_4-NH_3^+$). Owing to the low residual solubility of aminobenzoic acid, it is obtained here as a crystalline solid and can be isolated as such. This process has two significant drawbacks that are described below:

1. Adding a base to avoid a reduction in pH in the fermentation and adding an acid to reduce the pH in the subsequent crystallization results in continuous consumption of base and acid in the production process, which is associated with obvious economic drawbacks. The salt formed in the crystallization is dissolved in the mother liquor and has to be disposed of correspondingly.
2. The aminobenzoate present dissolved in the fermentation, in the case of excessive proportions by mass in the fermentation broth, can have an inhibiting effect on the metabolic activity of the bacteria, which reduces the further production of aminobenzoic acid or in the extreme case even stops it entirely.

SUMMARY

There was therefore still a need for further improvements in the field of fermentative production of aminobenzoic acid. Completely surprisingly, it has been found that the abovementioned problems can be solved, or at least reduced in terms of their effects, when (I) the aminobenzoic acid formed in the fermentation broth (present predominantly to completely as the anion, aminobenzoate) is bound partly, if appropriate as far as possible on account of the solubility equilibrium, as insoluble calcium aminobenzoate, then this insoluble calcium aminobenzoate is (II) isolated either as such or in a mixture with microorganisms and converted to a water-soluble form with separation of an insoluble calcium salt other than calcium aminobenzoate, and then (III) aminobenzoic acid is precipitated by introducing carbon dioxide under pressure into the aqueous solution freed of the precipitated calcium salt. This is shown in schematic form in the appended block diagram (cf. FIG. 1). Optional steps are indicated therein by dotted arrows or blocks. Expressions in bold type between parentheses that are used hereinafter refer to this diagram. The present invention accordingly provides a process for preparing aminobenzoic acid or an aminobenzoic acid conversion product, comprising the following steps:

(I) fermenting a raw material comprising at least
  a fermentable carbon-containing compound (C COMP.), preferably selected from starch hydrolyzate, sugarcane juice, sugarbeet juice, hydrolyzates of lignocellulose-containing raw materials or mixtures thereof (i.e. mixtures of two or more of the aforementioned compounds), and
  a nitrogen-containing compound (N COMP.), preferably selected from gaseous ammonia, aqueous ammonia, ammonium salts (especially inorganic ammonium salts such as ammonium chloride and/or ammonium sulfate, preferably ammonium sulfate), urea or mixtures thereof (i.e. mixtures of two or more of the aforementioned compounds),
  in a fermentation reactor using microorganisms and a calcium salt, especially an inorganic calcium salt (Ca SALT),
  so as to obtain a mixture, suspended in an aqueous fermentation solution, comprising undissolved microorganisms and precipitated calcium aminobenzoate (FERMENTATION BROTH) (FERMENTATION);

(II) (1) isolating the
  (1)(i) calcium aminobenzoate ($Ca(AB)_2$) or
  (1)(ii) mixture comprising undissolved microorganisms (MICROORGANISMS) and precipitated calcium aminobenzoate ($Ca(AB)_2$)
  obtained in step (I) from the aqueous fermentation solution—(ISOLATION), (2) converting the aminobenzoate bound in the calcium aminobenzoate to a water-soluble form to form a water-insoluble calcium salt other than calcium aminobenzoate by adding an aqueous phase (AQ) containing cations that form water-soluble aminobenzoate salts and anions that form water-insoluble calcium salts to the isolated calcium aminobenzoate from (1)(i) or to the isolated mixture comprising undissolved microorganisms and precipitated calcium aminobenzoate from (1)(ii),
  so as to obtain a suspension comprising
  (2)(i) the precipitated water-insoluble calcium salt ($CaX_2$ (s)) or
  (2)(ii) a mixture comprising undissolved microorganisms (MICROORGANISMS) and the water-insoluble calcium salt ($CaX_2$ (s)) in an aqueous solution of aminobenzoate ($AB^-(aq)$) (ION EXCHANGE), (3) separating the aqueous solution of aminobenzoate ($AB^-(aq)$) obtained in step (2) from the precipitated water-insoluble calcium salt from (2)(i) or from the mixture comprising undissolved microorganisms and the water-insoluble calcium salt from (2)(ii), preferably followed by recycling of the water-insoluble calcium salt from (2)(i) or of the mixture comprising undissolved microorganisms and the water-insoluble calcium salt from (2)(ii) into step (I) (SEPARATION);

(III) introducing carbon dioxide ($CO_2$) at a pressure of greater than or equal to $1.50\ bar_{(abs.)}$, preferably at a pressure in the range from $5.00\ bar_{(abs.)}$ to $100\ bar_{(abs.)}$, (more preferably at a pressure in the range from $7.00\ bar_{(abs.)}$ to $40.0\ bar_{(abs.)}$, most preferably at a pressure in the range from $20.0\ bar_{(abs.)}$ to $30.0_{(abs.)}$), into the aqueous solution of aminobenzoate separated off in step (II)(3) to separate aminobenzoic acid out, so as to form a suspension (AB-H+AQ) containing aminobenzoic acid (AB-H) in an aqueous solution (AQ) ($CO_2$ CRYSTALLIZATION);

(IV) isolating the aminobenzoic acid (AB-H) separated out in step (III), comprising lowering the pressure with release of carbon dioxide ($CO_2$) to give a carbon dioxide-depleted aqueous solution (AQ) that has been freed of aminobenzoic acid separated out (ISOLATION);

(V) using the aqueous solution (AQ) obtained in step (IV) that has been depleted of carbon dioxide and freed of aminobenzoic acid separated out as a constituent of the aqueous phase added in step (II)(2) (RECYCLING);

(VI) optionally further converting the aminobenzoic acid (AB-H) isolated in step (IV) to an aminobenzoic acid conversion product, with step (VI) preferably comprising one of the following conversions:
  (1) decarboxylating the aminobenzoic acid to give aniline;
  (2) decarboxylating the aminobenzoic acid to give aniline, followed by acid-catalyzed reaction of the aniline with formaldehyde to form di- and polyamines of the diphenylmethane series;
  (3) decarboxylating the aminobenzoic acid to give aniline, followed by acid-catalyzed reaction of the aniline with formaldehyde to form di- and polyamines of the diphenylmethane series, followed by reaction with phosgene to form di- and polyisocyanates of the diphenylmethane series;

(4) decarboxylating the aminobenzoic acid to give aniline, followed by conversion of the aniline to an azo compound;
(5) converting the aminobenzoic acid to an amide;
(6) converting the aminobenzoic acid to conductive polymers such as especially polyanthranilic acid—(SUBSEQUENT USES).

BRIEF DESCRIPTION OF THE DRAWINGS

Various features and characteristics of the inventions described in this specification may be better understood by reference to the accompanying figures, in which.

DETAILED DESCRIPTION

In the context of the present invention, the term "aminobenzoic acid conversion product" refers to a product obtained by further chemical conversion of aminobenzoic acid.

The fermentation takes place in an aqueous medium and affords a product mixture comprising solid constituents suspended in an aqueous solution. In the context of the present invention, this product mixture in its entirety, in accordance with the nomenclature customary in the technical literature, is referred to as fermentation broth. The fermentation broth is thus a biphasic mixture of in an aqueous solution and suspended insoluble solids. The suspended solids contain the microorganisms used (or at least a portion thereof) and precipitated calcium aminobenzoate. In the context of the present invention, the aqueous solution (i.e. the fermentation broth without the solid constituents suspended therein) is referred to as aqueous fermentation solution.

A fermentable carbon-containing compound is understood to mean any organic compound or mixture of organic compounds that can be used by the recombinant cells of the microorganism used to produce aminobenzoic acid (or, depending on the pH, aminobenzoate).

In the context of the present invention, the term water-insoluble or insoluble should of course not be understood in an absolute sense (since there is not even any such thing as absolute insolubility).

Thus, what is meant by the expression "converting the aminobenzoate bound in the calcium aminobenzoate to a water-soluble form to form a water-insoluble calcium salt other than calcium aminobenzoate by adding an aqueous phase containing cations that form water-soluble aminobenzoate salts and anions that form water-insoluble calcium salts" in step (II)(2) is of course not that all calcium ions without exception are precipitated as the salt of the anion added. What is instead meant is that the anions added form a calcium salt, the solubility product of which is sufficiently small to be exceeded under the given boundary conditions, and that the solubility product of the aminobenzoate salt of the cations used is sufficiently large not to be exceeded under the given boundary conditions. Therefore, aminobenzoate can go into solution and calcium ions "released" as a result can correspondingly be precipitated as salts of the anion added.

In the context of the present invention, pH values refer to the pH measured at 20° C., unless stated otherwise.

Figure 1:
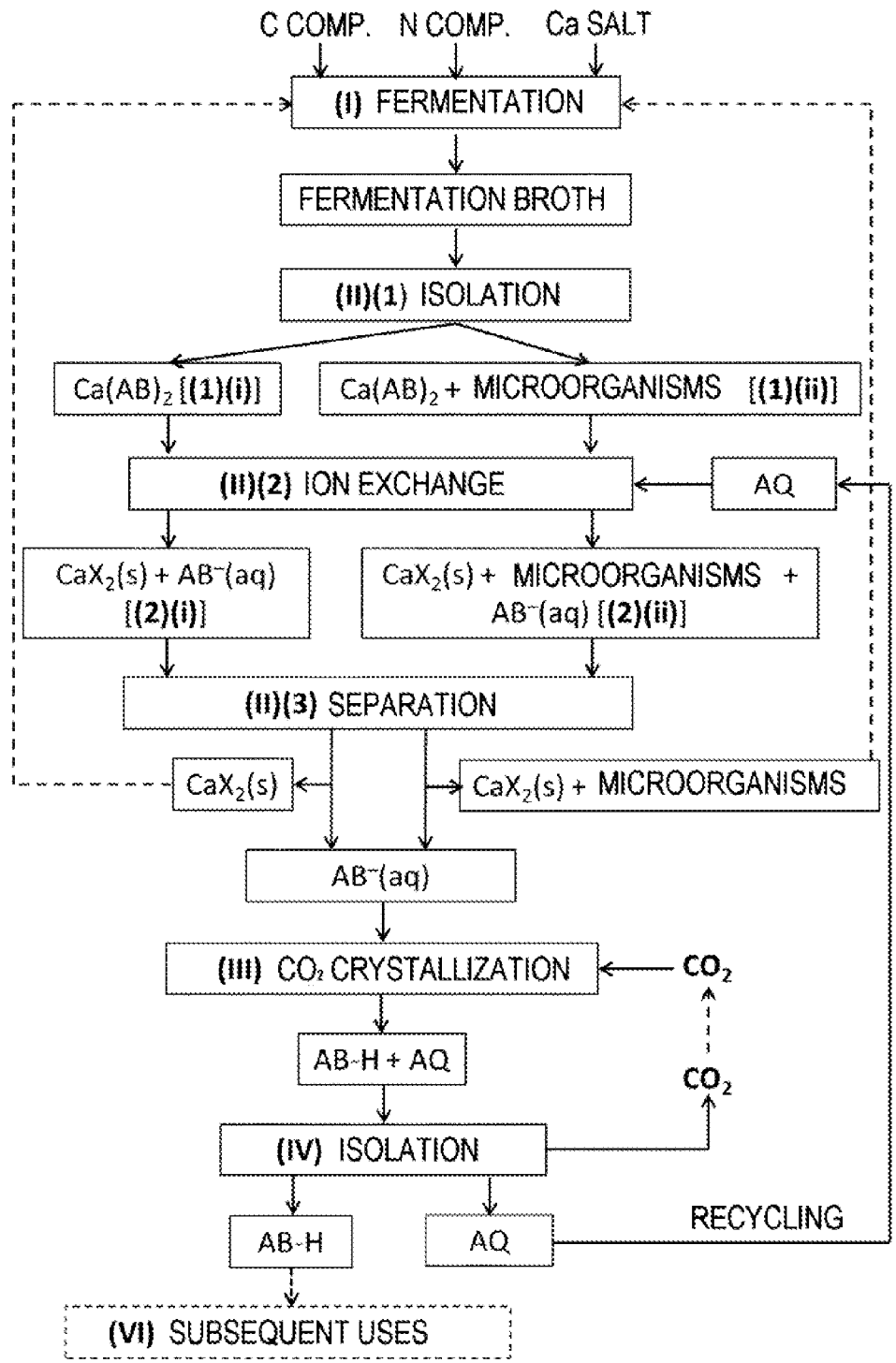
FIG. 1 shows a block diagram of the process of the invention. Steps that are optional in the broadest configuration of the invention are shown by dotted lines.

The figures that follow are appended for better understanding of the invention:

FIG. 1 shows a block diagram of the process of the invention. Steps that are optional in the broadest configuration of the invention are shown by dotted lines.

Figure 2:
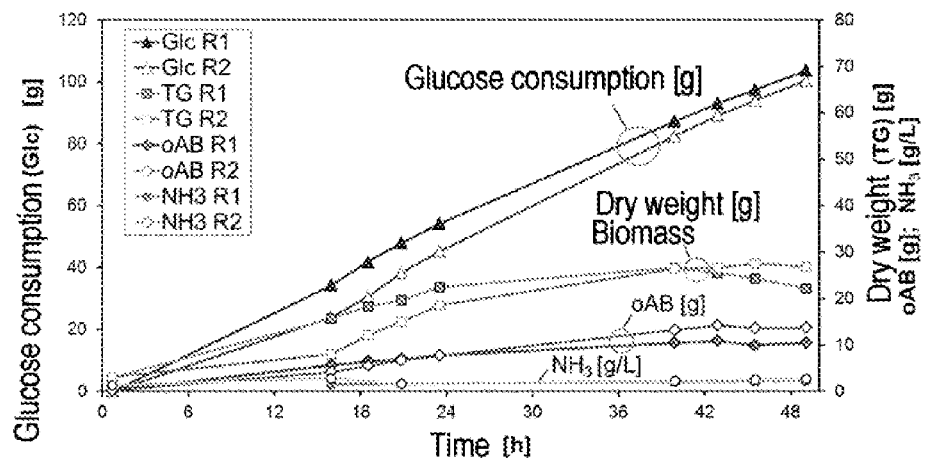
FIG. 2 shows a fed-batch fermentation of an ortho-aminobenzoate-producing strain of C. glutamicum according to the prior art. The experiment was conducted under otherwise identical conditions in two fermentation reactors in parallel. Filled symbols indicate reactor 1; open symbols indicate reactor 2.

FIG. 2 shows a fed-batch fermentation of an ortho-aminobenzoate-producing strain of C. glutamicum according to the prior art. The experiment was conducted under otherwise identical conditions in two fermentation reactors in parallel. Filled symbols indicate reactor 1; open symbols indicate reactor 2.

Figure 3:
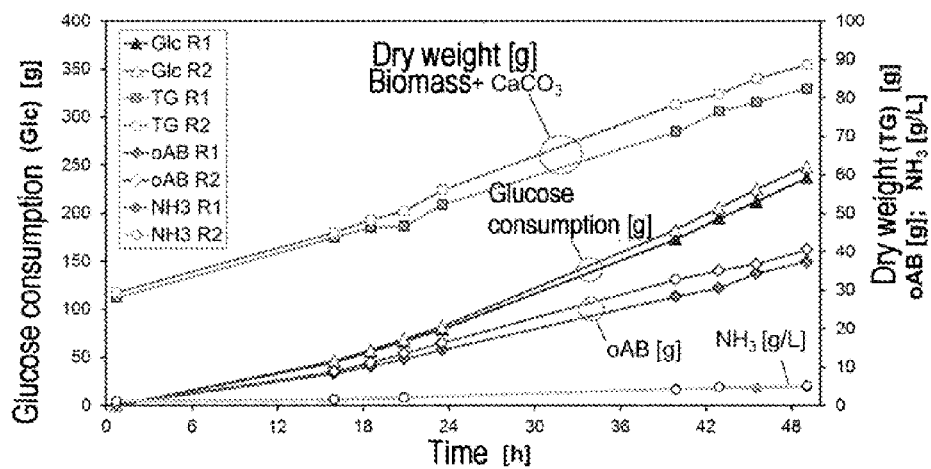
FIG. 3 shows a fed-batch fermentation of an ortho-aminobenzoate-producing strain of C. glutamicum in the presence of $CaCO_3$ according to step (I) of the present invention. The experiment was conducted under otherwise identical conditions in two fermentation reactors in parallel. Filled symbols indicate reactor 1; open symbols indicate reactor 2.

FIG. 3 shows a fed-batch fermentation of an ortho-aminobenzoate-producing strain of C. glutamicum in the presence of $CaCO_3$ according to step (I) of the present invention. The experiment was conducted under otherwise identical conditions in two fermentation reactors in parallel. Filled symbols indicate reactor 1; open symbols indicate reactor 2.

Figure 4:
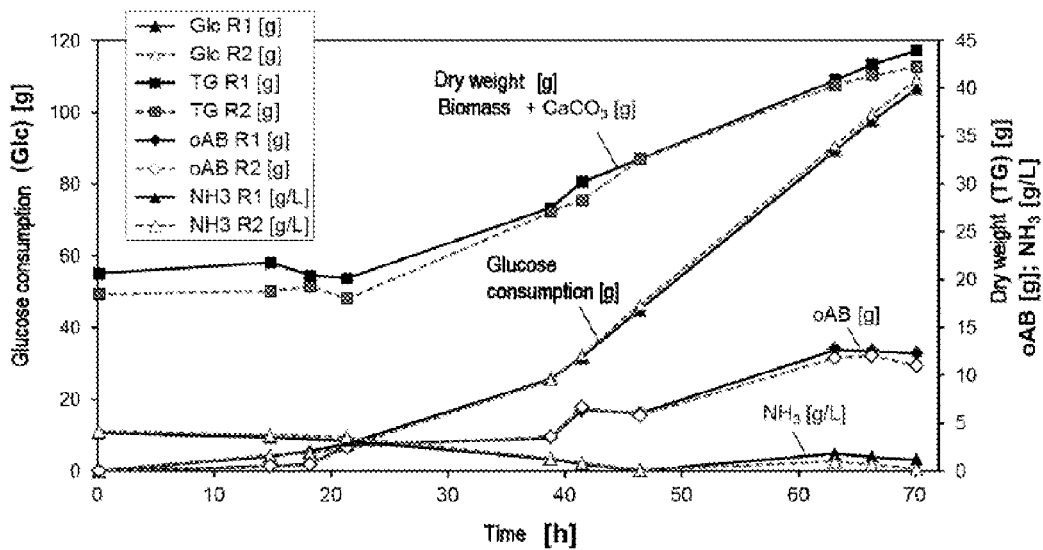
FIG. 4 and FIG. 5 show the results of a fed-batch fermentation of an ortho-aminobenzoate-producing strain of C. glutamicum in the presence of $CaCO_3$ according to step (I) of the present invention. The experiment was conducted under otherwise identical conditions in two fermentation reactors in parallel. Filled symbols indicate reactor 1; open symbols indicate reactor 2.
Figure 5:
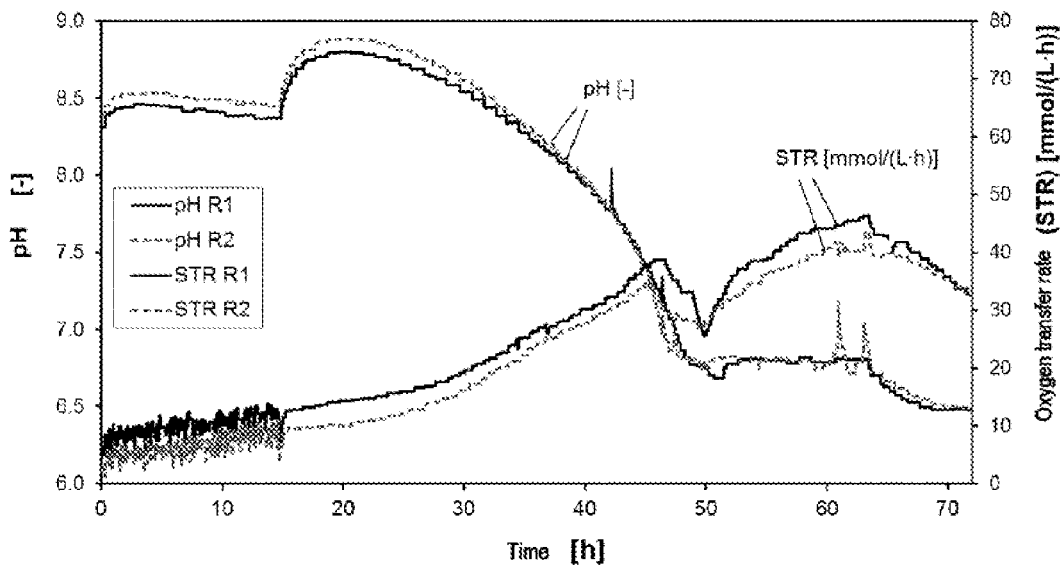

FIG. 4 and FIG. 5 show the results of a fed-batch fermentation of an ortho-aminobenzoate-producing strain of C. glutamicum in the presence of $CaCO_3$ according to step (I) of the present invention. The experiment was conducted under otherwise identical conditions in two fermentation reactors in parallel. Filled symbols indicate reactor 1; open symbols indicate reactor 2.

Figure 6:
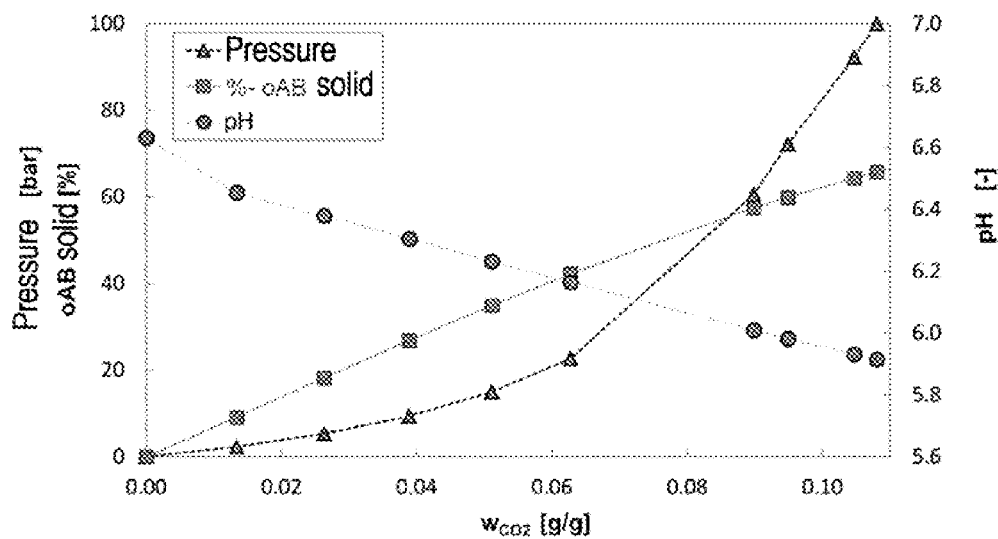
FIG. 6 shows the results of a simulation of the crystallization of ortho-aminobenzoic acid with CO2 in a closed vessel. Plotted on the primary axis are the pressure in bar and the precipitated proportion of anthranilic acid in % ($n_{oAB,solid}/n_{oAB,total} \times 100$) against the proportion by mass of $CO_2$ ($w_{co2}$) in the liquid phase. The secondary axis shows the progression of the pH. The symbols indicate points from the simulation; the dotted lines were added for improved visualization.

FIG. 6 shows the results of a simulation of the crystallization of ortho-aminobenzoic acid with $CO_2$ in a closed vessel. Plotted on the primary axis are the pressure in bar and the precipitated proportion of anthranilic acid in % ($no_{AB,solid}/n_{oAB,total} \times 100$) against the proportion by mass of $CO_2$ ($w_{CO2}$) in the liquid phase. The secondary axis shows the progression of the pH. The symbols indicate points from the simulation; the dotted lines were added for improved visualization.

Figure 7:
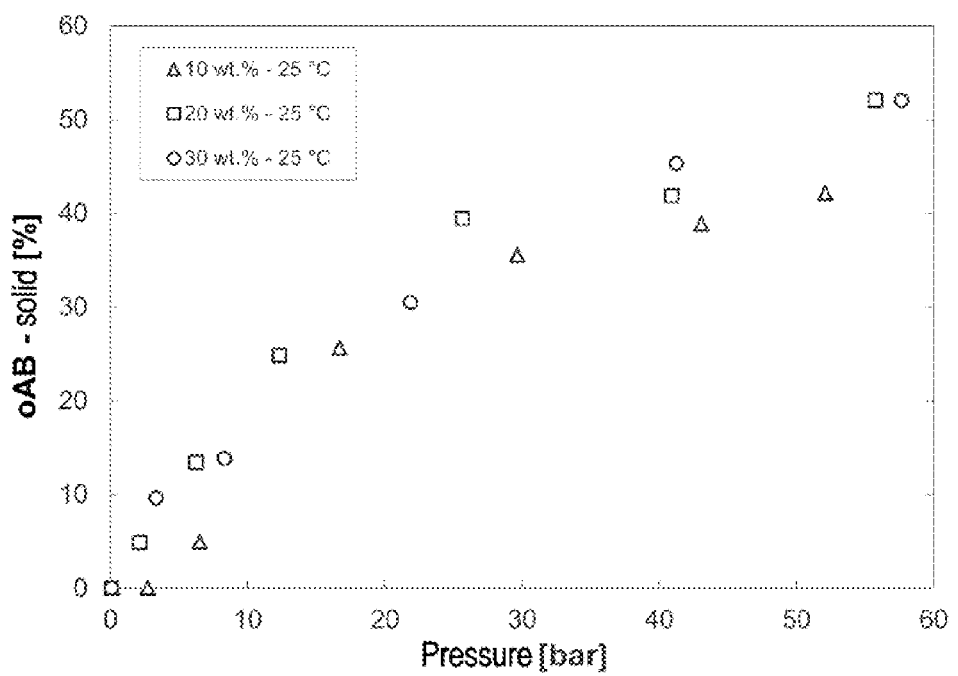
FIG. 7 shows the experimental results of a crystallization of ortho-aminobenzoic acid with $CO_2$ in a closed vessel. Plotted on the primary axis is the precipitated proportion of anthranilic acid in % ($n_{oAB,solid}/n_{oAB,total} \times 100$) against the pressure of $CO_2$ (bar). The initial concentrations of the NH4 ortho-aminobenzoate solutions were 10%, 20% and 30% by mass.

FIG. 7 shows the experimental results of a crystallization of ortho-aminobenzoic acid with $CO_2$ in a closed vessel. Plotted on the primary axis is the precipitated proportion of anthranilic acid in % ($no_{AB,solid}/n_{oAB,total} \times 100$) against the pressure of $CO_2$ (bar). The initial concentrations of the $NH_4$ ortho-aminobenzoate solutions were 10%, 20% and 30% by mass.

There follows firstly a brief summary of various possible embodiments.

In a first embodiment of the invention, which can be combined with all other embodiments, the calcium salt used in step (I) is selected from calcium carbonate, calcium hydrogencarbonate, calcium hydroxide, calcium oxide and mixtures thereof (i.e. mixtures of two or more of the aforementioned calcium salts), preference being given to using a mixture of calcium carbonate and calcium hydroxide as calcium salt.

In a second embodiment of the invention, which can be combined with all other embodiments, the aqueous phase added in step (II)(2) comprises
  lithium, sodium, potassium and/or ammonium cations, preferably ammonium cations, and
  carbonate and/or hydrogencarbonate anions.

In a third embodiment of the invention, which can be combined with all other embodiments, provided that these do not have a continuous configuration of the fermentation for their subject matter, the fermentation in step (I) is performed batchwise in fermentation cycles.

In a fourth embodiment of the invention, which is a particular configuration of the third embodiment, on conclusion of a fermentation cycle,
  step (II)(1) is conducted by discharging the aqueous fermentation solution obtained in step (I) from the fermentation reactor while retaining the mixture comprising undissolved microorganisms and precipitated calcium aminobenzoate suspended therein;
  step (II)(2) is conducted by introducing the aqueous phase into the fermentation reactor so as to obtain a suspension containing a mixture comprising undissolved microorganisms and the water-insoluble calcium salt in an aqueous solution of aminobenzoate in the fermentation reactor;
and
  step (II)(3) is conducted by discharging the aqueous solution of aminobenzoate obtained in step (II)(2) from the fermentation reactor, while retaining the mixture comprising undissolved microorganisms and the water-insoluble calcium salt and making it available for the next fermentation cycle.

In a fifth embodiment of the invention, which is another particular configuration of the third embodiment, on conclusion of a fermentation cycle,
  step (II)(1) is conducted by discharging the aqueous fermentation solution obtained in step (I) from the fermentation reactor together with the mixture comprising undissolved microorganisms and precipitated calcium aminobenzoate suspended therein and separating the mixture comprising undissolved microorganisms and precipitated calcium aminobenzoate from the aqueous fermentation solution outside the fermentation reactor and recycling it into the fermentation reactor;
  step (II)(2) is conducted by introducing the aqueous phase into the fermentation reactor so as to obtain a suspension containing a mixture comprising undissolved microorganisms and the water-insoluble calcium salt in an aqueous solution of aminobenzoate in the fermentation reactor;
and
  step (II)(3) is conducted by discharging the aqueous solution of aminobenzoate obtained in step (II)(2) from the fermentation reactor, while retaining the mixture comprising undissolved microorganisms and the water-insoluble calcium salt and making it available for the next fermentation cycle.

In a sixth embodiment of the invention, which is a further particular configuration of the third embodiment, on conclusion of a fermentation cycle,
  step (II)(1) is conducted by discharging the aqueous fermentation solution obtained in step (I) from the fermentation reactor together with the mixture comprising undissolved microorganisms and precipitated calcium aminobenzoate suspended therein and separating the mixture comprising undissolved microorganisms and precipitated calcium aminobenzoate from the aqueous fermentation solution outside the fermentation reactor and introducing it into a vessel other than the fermentation reactor;
  step (II)(2) is conducted by introducing the aqueous phase into this vessel so as to obtain a suspension containing a mixture comprising undissolved microorganisms and the water-insoluble calcium salt in an aqueous solution of aminobenzoate in this vessel;
and
  after the separation of the aqueous solution of aminobenzoate obtained in step (II)(2) from the mixture comprising undissolved microorganisms and the water-insoluble calcium salt in step (II)(3), this mixture separated off is introduced back into the fermentation reactor in a step (II)(4), hence making it available for the next fermentation cycle.

In a seventh embodiment of the invention, which can be combined with all other embodiments that have batchwise fermentation in fermentation cycles (step (I)) for their subject matter, steps (I) and (II) are repeated until the desired amount of aminobenzoic acid is obtained in step (IV) or the microorganisms used in step (I) have to be replaced.

In an eighth embodiment of the invention, which can be combined with all other embodiments, provided that these do not have a batchwise configuration of the fermentation for their subject matter, the fermentation in step (I) is performed continuously.

In a ninth embodiment of the invention, which is a particular configuration of the eighth embodiment, mixture suspended in the aqueous fermentation solution and comprising undissolved microorganisms and precipitated calcium aminobenzoate is discharged continuously from the fermentation reactor, and
  after discharging, step (II)(1) is conducted by separating the insoluble microorganisms and precipitated calcium aminobenzoate from one another and from the aqueous fermentation solution;
  step (II)(2) is conducted by adding the aqueous phase to the calcium aminobenzoate thus separated off;
wherein the insoluble microorganisms separated off in step (II)(1) are recycled partly to completely into the fermentation reactor.

In a tenth embodiment of the invention, which is another particular configuration of the eighth embodiment, precipitated calcium aminobenzoate suspended in the aqueous fermentation solution is discharged continuously from the fermentation reactor while retaining the undissolved microorganisms and after discharging, step (II)(1) is conducted by separating precipitated calcium aminobenzoate from the aqueous fermentation solution;

step (II)(2) is conducted by adding the aqueous phase to the calcium aminobenzoate thus separated off.

In an eleventh embodiment of the invention, which is a further particular configuration of the eighth embodiment, mixture suspended in the aqueous fermentation solution and comprising undissolved microorganisms and precipitated calcium aminobenzoate is discharged continuously from the fermentation reactor, and after discharging, step (II)(1) is conducted by separating the mixture comprising undissolved microorganisms and precipitated calcium aminobenzoate from the aqueous fermentation solution;

step (II)(2) is conducted by adding the aqueous phase to this mixture thus separated off;

and after the separation of the aqueous solution of aminobenzoate obtained in step (II)(2) from the mixture comprising undissolved microorganisms and the water-insoluble calcium salt in step (II)(3), this mixture separated off is introduced back into the fermentation reactor in a step (II)(4), so as to make it available for the further continuous fermentation therein.

In a twelfth embodiment of the invention, which is yet a further particular configuration of the eighth embodiment, mixture suspended in the aqueous fermentation solution and comprising undissolved microorganisms and precipitated calcium aminobenzoate is discharged continuously from the fermentation reactor, and after discharging, step (II)(1) is conducted by separating the mixture comprising undissolved microorganisms and precipitated calcium aminobenzoate from the aqueous fermentation solution;

step (II)(2) is conducted by adding the aqueous phase to this mixture thus separated off;

and after the separation of the aqueous solution of aminobenzoate obtained in step (II)(2) from the mixture comprising undissolved microorganisms and the water-insoluble calcium salt in step (II)(3), this mixture separated off is separated in a step (II)(4a) into the constituents of undissolved microorganisms and water-insoluble calcium salt, and, in a step (II)(4b), one of the constituents separated from one another, preferably the water-insoluble calcium salt, is returned to the fermentation reactor, where it is made available for the further continuous fermentation, preferably with addition of fresh microorganisms to the fermentation reactor.

In a thirteenth embodiment of the invention, which can be combined with all other embodiments, aminobenzoic acid is crystallized out of the aqueous fermentation solution obtained in step (II)(1) by adding acid until attainment of a pH in the range from 3.0 to <4.0 and the crystallized aminobenzoic acid is isolated, leaving an aminobenzoic acid-depleted mother liquor.

In a fourteenth embodiment of the invention, which is a particular configuration of the thirteenth embodiment, the aminobenzoic acid-depleted mother liquor is concentrated by a sequence of an adsorption step and a desorption step, wherein the desorption step is conducted by eluting with a desorbent of pH in the range from 6.0 to 11.0, wherein the desorbate thus obtained is optionally used as a further constituent of the aqueous phase added in step (II)(2).

In a fifteenth embodiment of the invention, which is a particular configuration of the fourteenth embodiment, the adsorbent used in the adsorption step is activated carbon.

In a sixteenth embodiment of the invention, which can be combined with all other embodiments, provided that they do not envisage the crystallization of aminobenzoic acid from the aqueous fermentation solution obtained in step (II)(1) by addition of acid, the step (II)(1) obtained aqueous fermentation solution is recycled into the fermentation from step (I).

In a seventeenth embodiment of the invention, which can be combined with all other embodiments, it is possible in step (III) to separate out only a portion, preferably 5.0% to 90%, of the aminobenzoate present in the aqueous solution obtained in step (II)(3) as aminobenzoic acid.

In an eighteenth embodiment of the invention, which can be combined with all other embodiments, step (IV) comprises the following partial steps:

(1) separating the aminobenzoic acid separated out and the aqueous solution from step (III) at a pressure equal to or greater than the pressure in step (III), (2) decompressing the aqueous solution separated off in step (1) to release carbon dioxide, giving a carbon dioxide-depleted aqueous solution.

In a nineteenth embodiment of the invention, which can be combined with all other embodiments, the water-insoluble calcium salt from (2)(i) that has been separated off in step (II)(3) or the mixture comprising undissolved microorganisms and the water-insoluble calcium salt from (2)(ii) is recycled into step (I).

In a twentieth embodiment of the invention, which can be combined with all other embodiments, the carbon dioxide released in step (IV) is collected and used in step (III).

In a twenty-first embodiment of the invention, which can be combined with all other embodiments, microorganisms of a type comprising *Escherichia coli*, *Pseudomonas putida*, *Corynebacterium glutamicum*, *Ashbya gossypii*, *Pichia pastoris*, *Hansenula polymorpha*, *Yarrowia lipolytica*, *Zygosaccharomyces bailii* or *Saccharomyces cerevisiae* are used in step (I), where the microorganisms used preferably consist solely of representatives of exactly one of these types, very particular preference being given to *Corynebacterium glutamicum* ATTC 13032.

In a twenty-second embodiment of the invention, which can be combined with all other embodiments, step (I) is conducted at a pH of 4.0 or greater, preferably at a pH in the range from 4.0 to 7.5, more preferably in the range from 5.0 to 7.0.

In a twenty-third embodiment of the invention, which can be combined with all other embodiments, preferably with the twenty-second, step (II)(2) is conducted at a pH of >7.0, preferably >8.0.

The embodiments briefly outlined above and further possible configurations of the invention are elucidated in detail hereinafter. The embodiments may be combined with one another as desired, unless the opposite is apparent from the context.

Step (I) of the process of the invention comprises the actual fermentation step, while the later steps comprise the workup and further processing of the product mixture formed in the fermentation.

Aminobenzoic acid occurs in three isomeric forms (ortho-, meta- and para-aminobenzoic acid). In principle, the process according to the invention can be applied to all three isomers, either in isomerically pure form or as mixtures of different isomers. For all embodiments of the present invention, it is the case that the aminobenzoic acid to be prepared by fermentation in step (I) preferably comprises the ortho isomer. The aminobenzoic acid to be prepared in step (I) more preferably comprises at least 50.0 mol %, even more preferably at least 90.0 mol %, based on the total molar amount of all aminobenzoic acid isomers present, of the ortho isomer. Very exceptionally preferably, the aminobenzoic acid to be provided in step (I) consists of the ortho isomer in isomerically pure form (i.e. isomeric purity>99.0 mol %).

The fermentation in step (I) is preferably conducted in such a way that the pH in the aqueous fermentation solution obtained does not go below a value of 4.0 since aminobenzoic acid is no longer adequately bound as the calcium salt at lower pH values—even if the microorganisms are suitable for the purpose. The pH established also depends on the type of calcium salt used, more specifically on the basicity of the counterion. Preferably, step (I) is conducted in such a way that a pH in the range from 4.0 to 7.5, preferably from 5.0 to 7.0, is established in the aqueous fermentation solution obtained. If required, the pH can be controlled by addition of aqueous or gaseous ammonia, aqueous potassium hydroxide or aqueous sodium hydroxide (when pH values are too low), or of hydrochloric acid, sulfuric acid or nitric acid (when pH values are too high). Different pH ranges within the ranges mentioned may be particularly optimal for different microorganisms; this is elucidated in detail hereinafter.

Preferred microorganisms for the performance of step (I) are bacteria or fungi, preferably yeasts. Particular preference is given here to microorganisms of a type selected from *Escherichia coli, Pseudomonas putida, Corynebacterium glutamicum, Ashbya gossypii, Pichia pastoris, Hansenula polymorpha, Yarrowia lipolytica, Zygosaccharomyces bailii* and *Saccharomyces cerevisiae*, preferably with use of no further microorganisms aside from these. The microorganisms used in step (I) especially preferably consist solely of representatives of exactly one of these species, with very exceptional preference for *Corynebacterium glutamicum* ATTC 13032. The pH to be maintained in the fermentation, as already mentioned, is guided by the microorganism used. Microorganisms such as *Corynebacterium glutamicum, Pseudomonas putida* or *Escherichia coli* are preferably cultured at neutral pH values (i.e. at a pH in the range from 6.0 to 7.5, preferably 6.0 to 7.0). Microorganisms such as *Saccharomyces cerevisiae*, by contrast, are preferably cultured in acidic medium (i.e. at a pH in the range from 4.0 to 6.0, preferably 5.0 to 6.0).

In each case, the microorganism from step (I) is preferably selected such that the ortho isomer of aminobenzoic acid is formed in the fermentation.

In a preferred configuration of the invention, bacteria are used as microorganisms. In this connection, reference is made in particular to patent applications WO 2015/124686 A1 and WO 2015/124687 A1, which describe fermentation processes using bacteria (see, for example, WO 2015/124687 A1, (i) page 15, line 8 to page 16, line 30, (ii) example 1 (page 29, lines 4 to 26), (iii) example 3 (especially page 34, lines 10 to 18), (iv) example 4 (especially page 55, lines 9 to 31). Preference is given to using bacteria capable of converting a fermentable carbon-containing compound to aminobenzoic acid in the presence of a suitable nitrogen source without the aminobenzoic acid thus formed being consumed straight away in intracellular biochemical processes, with the result that aminobenzoic acid is enriched in the cell and is ultimately transferred into the fermentation broth.

In another preferred configuration of the invention, yeasts are used as microorganisms. Reference is made here in particular to international patent application WO 2017/102853 A1. In particular, yeast cells are used which are capable of converting a fermentable carbon-containing compound to aminobenzoic acid in the presence of a suitable nitrogen source without the aminobenzoic acid thus formed being consumed straight away in intracellular biochemical processes, with the result that aminobenzoic acid is enriched in the cell and ultimately passes into the fermentation broth. Yeasts are preferably cultured in acidic medium (i.e. in the process of the invention at a pH in the range from 4.0 to 6.0, preferably 5.0 to 6.0).

Two routes are available in principle for obtaining a bacterium of this kind or a yeast of this kind, and these can also be combined in a preferred configuration:
  (i) The enzymatic reactions in the aminobenzoic acid metabolic pathway of the bacterial cell or yeast cell can be increased such that aminobenzoic acid is produced more rapidly than it is consumed.
  (ii) The conversion reactions which convert aminobenzoic acid to further metabolites or products (e.g. tryptophan) can be reduced or switched off, with the result that even the rate of aminobenzoic acid formation in wild-type strains is sufficient to lead to an enrichment of aminobenzoic acid in the cell.

Methods for obtaining bacteria or yeast cells with the properties specified above are known from the prior art. Suitable bacteria or yeast cells can be identified, for example, by screening for mutants which secrete aminobenzoic acid into the surrounding medium. However, preference is given to the specific modification of key enzymes by means of genetic engineering methods. Using customary genetic engineering methods, gene expression and enzyme activity can be enhanced, reduced or even completely suppressed as desired. Recombinant strains are the result.

More preferably, the bacteria or yeast cells which are capable of converting a fermentable carbon-containing compound to aminobenzoic acid in the presence of a nitrogen-containing compound contain a modification to the anthranilate phosphoribosyltransferase activity, which lowers said enzyme activity. As a result of said modification, the conversion of ortho-aminobenzoate to N-(5-phospho-D-ribosyl) anthranilate is reduced or completely suppressed. This causes enrichment of aminobenzoic acid in the cell. The expression "anthranilate phosphoribosyltransferase activity" refers here to an enzyme activity which catalyzes the conversion of ortho-aminobenzoate to N-(5-phospho-D-ribosyl) anthranilate.

In yeasts, anthranilate phosphoribosyltransferase activity is genetically encoded by the native gene TRP4 (YDR354W). In the bacterium *Corynebacterium glutamicum*, anthranilate phosphoribosyltransferase activity is encoded by the trpD gene (cg3361, Cg13032, NCgl2929). In the case of *Pseudomonas putida*, the encoding is effected via the trpD gene (PP_0421) within the trpDC operon.

The described lowering of anthranilate phosphoribosyltransferase activity can be achieved in principle in three ways:
  (i) The regulation of the expression of the gene for anthranilate phosphoribosyltransferase activity can be modified such that the transcription of the gene or subsequent translation is reduced or suppressed.

(ii) The nucleic acid sequence of the gene for anthranilate phosphoribosyltransferase activity can be modified such that the enzyme which is encoded by the modified gene has a lower specific activity.

(iii) The native gene for anthranilate phosphoribosyltransferase activity can be replaced with a different gene which originates from a different organism and encodes an enzyme having a specific anthranilate phosphoribosyltransferase activity lower than that of the native genes mentioned above (e.g. TRP4, trpD or trpDC).

Irrespective of which microorganism is used, the fermentation broth at the start of the fermentation in step (I) comprises recombinant cells of the microorganism used and at least one fermentable carbon-containing compound (and at least one nitrogen compound as nitrogen source). Preferably, the fermentation broth additionally contains further constituents selected from the group consisting of buffer systems, inorganic nutrients, amino acids, vitamins and further organic compounds which are required for the growth or housekeeping metabolism of the recombinant cells. The fermentation broth is water-based. After the fermentation process has been started, the fermentation broth also comprises aminobenzoic acid, the target fermentation product.

As already mentioned, a fermentable carbon-containing compound in the context of the present invention is understood to mean any organic compound or mixture of organic compounds that can be used to produce aminobenzoic acid by the recombinant cells of the microorganism used. The production of aminobenzoic acid can take place here in the presence or in the absence of oxygen.

Preference is given here to those fermentable carbon-containing compounds which can additionally serve as energy and carbon source for the growth of the recombinant cells of the microorganism used. Particularly suitable are starch hydrolyzate, sugarcane juice, sugarbeet juice and hydrolyzates of lignocellulose-containing raw materials. Likewise suitable are glycerol and C1 compounds, preferably carbon monoxide.

Irrespective of the microorganism used and the carbon and nitrogen source chosen, the calcium salt to be used in step (I) is preferably selected from calcium carbonate, calcium hydrogencarbonate, calcium hydroxide, calcium oxide or mixtures of two or more of the aforementioned compounds.

Especially preferred is the use of a mixture of calcium carbonate and calcium hydroxide. A suspension of calcium carbonate in water—since calcium carbonate goes partly into solution and the dissolved carbonate ions form hydrogencarbonate and hydroxide ions with water—always contains proportions of calcium hydroxide and is therefore encompassed by the wording "mixture of calcium carbonate and calcium hydroxide". The use of such calcium salts has the advantage that the addition of further bases, for example sodium hydroxide (see, for instance, the processes described in WO 2015/124686 A1 and WO 2015/124687 A1), as buffer is required in a reduced amount at most, if at all. Calcium carbonate may be initially charged in the fermentation reactor in solid form. Addition as an aqueous suspension is also possible. Calcium oxide may in principle likewise be introduced into the fermentation reactor in solid form. If calcium oxide is available as calcium source, however, it is preferable first to quench it with water and hence convert it to calcium hydroxide. Calcium hydroxide and calcium hydrogencarbonate are preferably metered in in the form of aqueous solutions.

The fermentation of the invention (step (I)) is, as already mentioned, preferably conducted at pH values in the range from 4.0 to 7.5, preferably 5.0 to 7.0. Under these pH conditions, it is also possible for calcium ions to go at least partly into solution from calcium salts that are insoluble under other conditions, and these are then capable of complexing and precipitating aminobenzoate formed. In this way, calcium salts such as calcium carbonate also go gradually into solution in that case (forming carbon dioxide from the carbonate ions in the case of calcium carbonate, which—at least partly—outgases).

The calcium salt to be used in step (I) is preferably used in at least a stoichiometric amount based on the amount of aminobenzoic acid expected to be produced. It is also possible to use an excess, for example a molar ratio of calcium ions to the expected amount of aminobenzoic acid produced of 1:1 or more.

In one embodiment of the invention, step (I) is performed continuously, i.e. the reactants are fed continuously to the fermentation reactor and the product is withdrawn continuously from the fermentation reactor. The product withdrawn continuously from the fermentation reactor, in the simplest case, is the mixture suspended in the aqueous fermentation solution, comprising undissolved microorganisms and precipitated calcium aminobenzoate, i.e. the fermentation broth. However, it is also conceivable, by use of suitable separation methods, to retain the microorganisms selectively in the fermentation reactor and to discharge solely an aqueous suspension of calcium aminobenzoate. Such a separation is preferably effected by exploiting the different densities of calcium aminobenzoate and microorganisms, for example in a flotation method, in which case the microorganisms "float" on the surface, or using centrifugation.

In another embodiment of the invention, step (I) is conducted in a discontinuous process regime ("batchwise mode") in fermentation cycles. A fermentation cycle preferably comprises the initial charging or addition of microorganisms to a culture medium, the initial charging and/or addition of nutrients, the buildup of microorganisms, the formation of the desired product, i.e. the aminobenzoic acid, and the complete or partial emptying of the reactor on conclusion of the fermentation. In one variant of the batchwise mode of operation (called "fed-batch mode"), the reactants are fed continuously to the fermentation reactor for as long as the reactor volume allows it without products—possibly excluding gaseous constituents that are discharged to an offgas system via a reactor connection—being withdrawn from the reactor. The reaction is stopped after addition of the maximum possible amount of reactants and the product mixture is withdrawn from the fermentation reactor. Details of these modes of operation that are merely outlined briefly at this point are elucidated further down.

Irrespective of the exact mode of operation, the fermentation reactor preferably comprises devices for measuring important process parameters such as temperature, pH, concentration of substrate and product, dissolved oxygen content, and cell density of the fermentation broth. In particular, the fermentation reactor preferably comprises devices for adjusting at least one (preferably all) of the aforementioned process parameters.

Suitable fermentation reactors are stirred tanks, membrane reactors, plug flow reactors or loop reactors (see for example Bioprozesstechnik, Horst Chmiel, ISBN-10: 3827424763, Spektrum Akademischer Verlag). Particularly preferred for both aerobic and anaerobic fermentations are stirred tank reactors and loop reactors (preferably airlift reactors in which circulation of the liquid in the reactor is achieved by sparging).

In step (II) of the process of the invention, the calcium aminobenzoate precipitated in step (I) is first isolated from the aqueous fermentation solution in a first step, step (II)(1). This is accomplished either selectively, i.e. with separation of the undissolved microorganisms as well, or non-selectively, meaning that the mixture of the solid constituents of the fermentation broth containing the undissolved microorganisms and precipitated calcium aminobenzoate is separated from the aqueous fermentation solution as an unchanged totality. The latter can be brought about by a simple filtration, sedimentation or centrifugation. Selective separation is possible, for example, by exploiting the different densities of calcium aminobenzoate and microorganisms, for instance in a flotation method, in which case the microorganisms "float" on the surface, or in a centrifugation method. As already elucidated in connection with step (I), such a separation of microorganisms from calcium aminobenzoate can also be effected by retaining the microorganisms in the fermentation reactor.

The aqueous fermentation solution remaining in step (II)(1) after the isolation of the calcium aminobenzoate has a pH of preferably 4.0 or more, depending on the exact conditions of the fermentation. Since this aqueous fermentation solution can still contain proportions of dissolved aminobenzoate, it is advantageously possible to crystallize aminobenzoic acid out of it by addition of acid until a pH in the range from 3.0 to <4.0 is attained, and to isolate the crystallized aminobenzoic acid, leaving a mother liquor depleted of aminobenzoic acid. Suitable acids for this purpose are preferably mineral acids such as sulfuric acid, phosphoric acid or hydrochloric acid; hydrochloric acid and sulfuric acid are particularly preferred. The mother liquor obtained still contains residual contents of aminobenzoic acid. It is therefore preferable to concentrate this mother liquor by a sequence of an adsorption step and a desorption step. The desorption step can be conducted here by elution with a desorbent of pH in the range from 6.0 to 11.0, and the desorbate thus obtained can advantageously be used as a constituent of the aqueous phase added in step (II)(2). In another embodiment, the desorption is conducted in a strongly acidic range (i.e. the desorbent has a pH of less than 3.0), and the desorbate is subjected to a post-crystallization by increasing the pH to a value of ≥3.0, preferably to a value in the range from 3.0 to <4.0. An example of a suitable adsorbent usable in the adsorption step is activated carbon.

It may be advisable to decolorize the aqueous fermentation solution remaining after the isolation of the calcium aminobenzoate in step (II)(1) prior to the crystallization and/or the mother liquor obtained in the crystallization prior to the adsorption. In one embodiment, this decolorization is preferably conducted in such a way that the aqueous fermentation solution or mother liquor is passed through a column containing solid packing, in order to remove dyes by means of adsorption. A possible solid phase which can be used is, for example, kieselguhr, activated carbon or ion-exchange packing. In another embodiment, the decolorization is conducted by stirring with pulverulent activated carbon or pulverulent kieselguhr, followed by filtration.

In principle, it is also conceivable, rather than a crystallization, to recycle the aqueous fermentation solution remaining after the isolation of the calcium aminobenzoate in step (II)(1) partly into the fermentation from step (I). Owing to the associated dilution of the reaction mixture, however, the embodiment with crystallization is generally preferable.

In step (II)(2), the aminobenzoate bound in the calcium aminobenzoate isolated in step (II)(1) is released by conversion to a water-soluble form (ion exchange step). This is preferably accomplished by admixing the process product (i.e. either calcium aminobenzoate or a mixture containing calcium aminobenzoate and undissolved microorganisms) obtained in step (II)(1) with an aqueous phase comprising
  lithium, sodium, potassium and/or ammonium cations, preferably ammonium cations, and
  carbonate and/or hydrogencarbonate anions.

Particular preference is given here to a solution of ammonium carbonate. Aminobenzoate goes into solution here as the salt of the cation introduced, while the anion introduced is precipitated as the calcium salt. The ion exchange step is typically effected at ambient temperature within a few minutes. Intimate mixing of the aqueous phase added with the calcium aminobenzoate, for instance by vigorous stirring, is advantageous. It is not necessary for all the aminobenzoate bound in the calcium aminobenzoate to be dissolved in step (II)(2); any remaining undissolved residual constituents may be recycled in the subsequent step (II)(3), as described therein, into step (I). This does not leave the scope of the invention.

Step (II)(2) is preferably conducted at a pH of >7.0, preferably >8.0. If such a pH is not established of its own accord under the process conditions chosen, it is appropriate to add base, preferably aqueous or gaseous ammonia.

In step (II)(3), the process product obtained in step (II)(2) (i.e. the precipitated solid—either the water-insoluble calcium salt [(2)(i)] or the mixture containing the water-insoluble calcium salt and undissolved microorganisms [(2)(ii)]—suspended in an aqueous solution containing the aminobenzoate that has gone into solution) is separated into its solid and liquid constituents, and it is optionally also possible to undertake a separation of calcium salt [(2)(i)] and undissolved microorganisms [(2)(ii)]. In each case, it is possible to use the same separation techniques as described above for step (II)(1). In all embodiments of the invention, it is preferable to recycle the solid separated off in step (II)(3) into step (I), since it can serve to provide the calcium salt in an advantageous manner therein. If not all the aminobenzoate bound in the calcium aminobenzoate has gone into solution in the preceding step, undissolved calcium aminobenzoate remains in this solid and is recycled therewith into step (I), such that no losses occur.

In step (III), aminobenzoic acid is separated out by introducing carbon dioxide under elevated pressure into the aqueous solution of aminobenzoate obtained in step (II)(3) (crystallization step). Through the injection of carbon dioxide, as a result of the formation of protolysis equilibria, there is a decrease in the pH into a range in which aminobenzoate is converted to aminobenzoic acid, which precipitates out owing to its low solubility in aqueous media. Preference is therefore given to introducing carbon dioxide until a pH of 5.0 or lower has been established. It is not absolutely necessary to quantitatively separate out aminobenzoic acid at this point owing to the inventive recycling of step (V). In a preferred configuration of the invention, the procedure is as follows:

The aqueous solution of aminobenzoate obtained in step (II)(3) is admixed with carbon dioxide, especially in such a way that only a portion, preferably 5.0% to 90%, of the aminobenzoate crystallizes out as an acid. The precipitated acid is isolated by filtration, preferably at the same pressure under which the carbon dioxide has been injected (pressure filtration). The remaining filtrate is decompressed (preferably to ambient pressure), with partial outgassing of carbon dioxide. Even after the decompression, the filtrate still contains carbonate ions and residual amounts of aminobenzoate (with the cation that forms water-soluble aminobenzoate salts which has been introduced in step (II)(2) as counterion). This filtrate is returned to the ion exchange step (II)(2). Since step (II)(2) is constantly supplied with new calcium aminobenzoate via step (II)(1), the proportion of aminobenzoic acid removed by crystallization is replaced in this way.

In step (IV), the aminobenzoic acid crystallized in step (III) is separated off (isolation step). Step (IV) also comprises lowering the pressure with release of carbon dioxide, such that the process product obtained from this step is a carbon dioxide-depleted aqueous solution that has been freed of separated-out aminobenzoic acid. As already mentioned, not necessarily all the aminobenzoate is precipitated out as the acid in the preceding step Aminobenzoate ions remaining in solution are not separated off as well in step (IV).

Irrespective of the exact configuration of this step, carbon dioxide is obtained, which can advantageously be collected and used for a new addition in step (III). This leads to an economically and environmentally very advantageous circulation regime.

This step (IV) preferably comprises the following partial steps:
(1) separating the aminobenzoic acid and the aqueous solution from step (III) at a pressure equal to or greater than the pressure in step (III),
(2) decompressing the aqueous solution obtained in step (1) to release carbon dioxide, giving a carbon dioxide-depleted aqueous solution. The carbon dioxide released in the decompression can be collected and used for a new addition in step (III).

In step (1), the aminobenzoic acid separated out in the preceding step is separated from the aqueous solution. Methods for this purpose are known per se from the prior art. According to the invention, said step is preferably carried out by filtration or centrifugation. Preferably, said step is carried out as described in WO 2015/124687 A1. Reference is made here in particular to WO 2015/124687 A1, page 17, line 13 to page 17, line 16. The filtration is effected here at elevated pressure in order to avoid premature degassing of carbon dioxide. Centrifugation can be conducted with standard centrifuges (likewise under pressure). It is also possible to leave the suspension obtained in the first step standing until the precipitated crystals of aminobenzoic acid settle out, in order then to decant or suction off the supernatant mother liquor under pressure.

The aminobenzoic acid thus obtained can optionally be purified further. This partial step of step (IV) is known per se from the prior art (see, in particular, WO 2015/124687 A1 and especially to WO 2015/124687 A1, page 18, line 4 to page 18, line 6) and is preferably carried out by one or more washes with aqueous wash media, preferably water. In order to avoid yield losses, the pH of the aqueous wash medium is preferably adjusted to a value in the range from 3.0 to <4.0, preferably to a value of 3.5.

In step (V), the aqueous solution that has been freed of separated-out aminobenzoic acid and remains in step (IV) after the aminobenzoic acid has been separated off is recycled into step (II)(2), where it is used as a constituent of the aqueous phase (AQ) to be used in this step (recycling step). The wording "is used as a constituent of the aqueous phase to be used in this step" also includes the case that the aqueous solution that has been freed of separated-out aminobenzoic acid and remains in step (IV) after the aminobenzoic acid has been separated off is the sole constituent of the aqueous phase to be used in step (II)(2). It is thus possible in accordance with the invention that—apart from variations from the regular operation of the process, for example in the case of startup operations—the aqueous phase (AQ) containing cations that form water-soluble aminobenzoate salts and water-insoluble calcium salts is provided solely by this recycling according to step (V). Any pH adjustments required, as elucidated further up in connection with the discussion of step (II)(2), are of course unaffected by this; i.e. are also possible when the aqueous phase AQ is being provided solely by recycling.

The process of the invention thus enables an extremely advantageous circulation regime.

Particularly advantageous chemical engineering configurations of the process of the invention are outlined hereinafter:

Batchwise Process Regime

In a first variant of the batchwise process regime already mentioned further up, on conclusion of a fermentation cycle,
 step (II)(1) is conducted by discharging the aqueous fermentation solution obtained in step (I) from the fermentation reactor while retaining the mixture comprising undissolved microorganisms and precipitated calcium aminobenzoate suspended therein;
 step (II)(2) is conducted by introducing the aqueous phase into the fermentation reactor so as to obtain a suspension containing a mixture comprising undissolved microorganisms and the water-insoluble calcium salt in an aqueous solution of aminobenzoate in the fermentation reactor; and
 step (H)(3) is conducted by discharging the aqueous solution of aminobenzoate obtained in step (II)(2) from the fermentation reactor, while retaining the mixture comprising undissolved microorganisms and the water-insoluble calcium salt and making it available for the next fermentation cycle.

In a second variant of the batchwise process regime, on conclusion of a fermentation cycle,
 step (II)(1) is conducted by discharging the aqueous fermentation solution obtained in step (I) from the fermentation reactor together with the mixture comprising undissolved microorganisms and precipitated calcium aminobenzoate suspended therein and separating the mixture comprising undissolved microorganisms and precipitated calcium aminobenzoate from the aqueous fermentation solution outside the fermentation reactor and then recycling the mixture of solids thus separated off into the fermentation reactor;
 step (II)(2) is conducted by introducing the aqueous phase into the fermentation reactor so as to obtain a suspension containing a mixture comprising undissolved microorganisms and the water-insoluble calcium salt in an aqueous solution of aminobenzoate in the fermentation reactor; and
 step (II)(3) is conducted by discharging the aqueous solution of aminobenzoate obtained in step (II)(2) from the fermentation reactor, while retaining the mixture comprising undissolved microorganisms and the water-insoluble calcium salt and making it available for the next fermentation cycle.

Finally, in a third variant of the batchwise process regime, on conclusion of a fermentation cycle,
- step (II)(1) is conducted by discharging the aqueous fermentation solution obtained in step (I) from the fermentation reactor together with the mixture comprising undissolved microorganisms and precipitated calcium aminobenzoate suspended therein and separating the mixture comprising undissolved microorganisms and precipitated calcium aminobenzoate from the aqueous fermentation solution outside the fermentation reactor and introducing it into a vessel other than the fermentation reactor;
- step (II)(2) is conducted by introducing the aqueous phase into this vessel so as to obtain a suspension containing a mixture comprising undissolved microorganisms and the water-insoluble calcium salt in an aqueous solution of aminobenzoate in this vessel;
- wherein, in addition,
- after the separation of the aqueous solution of aminobenzoate obtained in step (II)(2) from the mixture comprising undissolved microorganisms and the water-insoluble calcium salt in step (II)(3), this mixture separated off is introduced back into the fermentation reactor in a step (II)(4), such that it is made available for the next fermentation cycle.

Irrespective of the exact configuration of the batchwise process, it is preferable to repeat steps (I) and (II) until the desired amount of aminobenzoic acid is obtained in step (IV) or the microorganisms used in step (I) have to be replaced owing to their exhaustion. This mode of operation can be implemented either in the form of a "batchwise mode" (owing to the repetitions of the individual steps, more specifically: "repeated batchwise mode") or of a "fed-batch mode" (owing to the repetitions of the individual steps, more specifically: "repeated fed-batch mode").

Continuous Process Regime

In a first variant of the continuous process regime already mentioned further up, fermentation broth is withdrawn continuously from the fermentation reactor, i.e. the mixture suspended in the aqueous fermentation solution and comprising undissolved microorganisms and precipitated calcium aminobenzoate. In this case,
- step (II)(1) is conducted by, after discharge of fermentation broth, separating the insoluble microorganisms and precipitated calcium aminobenzoate from one another and from the aqueous fermentation solution;
- step (II)(2) is conducted by adding the aqueous phase to the calcium aminobenzoate thus separated off;
- wherein, in addition, the insoluble microorganisms separated off in step (II)(1) are recycled partly to completely into the fermentation reactor.

In a second variant of the continuous process regime already mentioned further up, precipitated calcium aminobenzoate suspended in the aqueous fermentation solution is removed continuously from the fermentation reactor without the insoluble microorganisms, meaning that only the microorganisms are separated off at first in step (II)(1) and remain in the fermentation reactor. After discharging the suspension of calcium aminobenzoate in aqueous fermentation solution, the precipitated calcium aminobenzoate is then separated from the aqueous fermentation solution. Step (II)(2) is conducted by adding the aqueous phase to the calcium aminobenzoate thus separated off. The second variant is thus a variant of the first variant, which differs in that the separation of microorganisms and calcium aminobenzoate is already conducted in the fermentation reactor.

In a third variant of the continuous process regime already mentioned further up, fermentation broth is withdrawn continuously from the fermentation reactor as in the first variant, i.e. the mixture suspended in the aqueous fermentation solution and comprising undissolved microorganisms and precipitated calcium aminobenzoate. In this case, step (II)(1) is conducted by, after discharge of the fermentation broth, separating the mixture comprising undissolved microorganisms and precipitated calcium aminobenzoate from the aqueous fermentation solution;
- step (II)(2) is conducted by adding the aqueous phase to this mixture thus separated off;
- wherein, in addition,
- after the separation of the aqueous solution of aminobenzoate obtained in step (II)(2) from the mixture comprising undissolved microorganisms and the water-insoluble calcium salt in step (II)(3), this mixture separated off is introduced back into the fermentation reactor in a step (II)(4) and made available for the further continuous fermentation.

In a fourth variant of the continuous process regime already mentioned further up, the procedure is at first as in the third variant, except that, by contrast, the mixture separated off in step (II)(3) is first separated in a step (II)(4a) into its essential constituents, i.e. into undissolved microorganisms and water-insoluble calcium salt, and then, in a step (II)(4b), only one of the constituents thus separated, preferably the water-insoluble calcium salt, is introduced back into the fermentation reactor. This is advisable especially when the microorganisms from step (II)(3) are already exhausted and have to be replaced by fresh microorganisms.

In the above-described step (IV), the aminobenzoic acid is obtained in electrically neutral form. In this form, it can be supplied directly to the optional (and preferred) conversion to an aminobenzoic acid conversion product in step (VI). Selected further conversions of the aniline obtained in step (VI) are:
(1) decarboxylating the aminobenzoic acid to give aniline;
(2) decarboxylating the aminobenzoic acid to give aniline, followed by acid-catalyzed reaction of the aniline with formaldehyde to form di- and polyamines of the diphenylmethane series;
(3) decarboxylating the aminobenzoic acid to give aniline, followed by acid-catalyzed reaction of the aniline with formaldehyde to form di- and polyamines of the diphenylmethane series, followed by reaction with phosgene to form di- and polyisocyanates of the diphenylmethane series;
(4) decarboxylating the aminobenzoic acid to give aniline, followed by conversion of the aniline to an azo compound;
(5) converting the aminobenzoic acid to an amide;
(6) converting the aminobenzoic acid to a conductive polymer such as preferably polyanthranilic acid.

The decarboxylation of the aminobenzoic acid to give aniline (VI)(1) is known per se and can be performed by any prior art process. Preference is given to the following procedure:

Step (VI)(1) can be performed in all reactor types that are customary in chemical engineering and familiar to the person skilled in the art, for example
- stirred tank reactors,
- continuous stirred tank reactors,
- tubular reactors, preferably with a fixed catalyst bed, or
- slurry phase reactors (also called suspension reactors) with catalyst recirculation or catalyst recovery.

It is also possible to connect multiple reactors in series to give a reactor cascade, i.e. the liquid product discharge of one reactor flows into the next reactor for further completion of the conversion.

The decarboxylation of step (VI)(1) proceeds readily in the presence of a catalyst. Catalysts suitable for the performance of step (VI)(I) are catalysts familiar to the person skilled in the art, for example aqueous acids such as sulfuric acid, nitric acid and hydrochloric acid; solid acids such as zeolites and Si—Ti molecular sieves, solid bases such as hydroxyapatite and hydrotalcite; polymeric acids such as ion exchange resins (preferably Amberlyst). If the catalyst is used in the form of particles or in powder form, a preferred embodiment of the invention involves slurrying the catalyst in the liquid reaction mixture, preferably by stirring. Particularly suitable for this purpose is a slurry phase reactor (also called suspension reactor), wherein the catalyst is used in a concentration in the range from 0.100% by mass to 50.0% by mass, preferably in the range from 10.0% by mass to 30.0% by mass, based on the total mass of the liquid reaction mixture. In another preferred embodiment, the catalyst is arranged in a catalyst bed in a tubular reactor, wherein the catalyst, preferably in the form of particles (e.g. spheres) in this embodiment, is preferably fixed in the catalyst bed, for example arranged between sieve plates. Irrespective of the type of reactor used, the catalyst used in step (VI)(1) is preferably a zeolite catalyst, more preferably a zeolite of type Y in protonated form (H form). The arrangement of the catalyst, preferably in particle form, in a fixed bed is of course not restricted to tubular reactors, but can in principle also be applied to stirred reactors. Furthermore, it is possible to use the catalyst in monolithic form.

In the decarboxylation of step (VI)(1), it is possible to observe the following reaction parameters, for example:
  temperature preferably in the range from 140° C. to 240° C. and pressure preferably in the range from 1.00 $bar_{(abs.)}$ to 20.0 $bar_{(abs.)}$,
  temperature more preferably in the range from 160° C. to 220° C. and pressure more preferably in the range from 1.00 bar(abs.) to 15.0 bar(abs.),
  temperature most preferably at a temperature in the range from 180° C. to 200° C. and pressure most preferably in the range from 4.00 $bar_{(abs.)}$ to 10.0 $bar_{(abs.)}$.

The stream containing aniline, prior to its withdrawal from the reactor, preferably passes through a filter in order to prevent solid particles (e.g. catalyst particles) from being entrained.

The aminobenzoic acid to be decarboxylated is preferably used in solution for the performance of step (VI)(1). Suitable solvents are water or organic solvents such as 1-dodecanol or—see above—aniline.

Step (VI)(1) is preferably carried out continuously, i.e. the aminobenzoic acid to be decarboxylated is fed continuously to the reactor and the product is withdrawn continuously from the reactor. In one variant of this procedure, at least some of the catalyst is also exchanged in the continuous operation, constantly or at intervals, in order to prevent its performance capacity from being exhausted. Alternatively, a discontinuous process regime (called "batchwise mode") is possible. In one variant of the discontinuous mode of operation (called "fed-batch mode"), the reactants are fed continuously to the reactor as long as the reactor volume allows it without products being withdrawn from the reactor. The reaction is interrupted after addition of the maximum possible amount of reactants and the product mixture is withdrawn from the reactor.

In an alternative preferred embodiment, another feasible process regime is one in which aminobenzoic acid to be decarboxylated is fed continuously to the reactor and the product is withdrawn continuously from the reactor, but consumed catalyst is not withdrawn in the continuous operation and, instead, fresh catalyst is added (either constantly or at intervals) until the maximum catalyst amount predetermined by the available reactor volume has been reached in the reactor, and the reactor is then taken out of operation for the purposes of cleaning and catalyst exchange.

In all embodiments, preference is given to conducting step (VI)(1) with exclusion of oxygen. Suitable gases for inertization of the reactor are inert gases such as nitrogen, carbon dioxide or noble gases.

The crude aniline withdrawn from the reactor of step (VI)(1) is preferably purified before it is used further. This purification can be effected by processes familiar to the person skilled in the art. The purification preferably includes at least one distillation step, which may be preceded by removal of water by phase separation. The purification may also include a base treatment for removing acidic impurities before, during or after the distillation step. Suitable configurations are, for example, described in EP-A-1 845 079, EP-A-1 845 080, EP-A-2 263 997 and EP-A-2 028 176. (These documents are concerned with the purification of aniline which has been obtained by hydrogenation of nitrobenzene; the described steps for purifying the crude aniline are, however, also applicable to aniline produced in other ways.)

The further reaction of thus-obtained aniline with formaldehyde to give di- and polyamines of the diphenylmethane series (VI)(2) is known per se and may be performed by any prior art method.

The continuous or partially discontinuous preparation of di- and polyamines of the diphenylmethane series from aniline and formaldehyde is, for example, disclosed in EP 1 616 890 A1, U.S. Pat. No. 5,286,760, EP-A-451442 and WO-A-99/40059. The reaction is effected under acid catalysis. A suitable acidic catalyst is preferably hydrochloric acid.

The further reaction of the di- and polyamines of the diphenylmethane series thus obtained with phosgene to give di- and polyisocyanates of the diphenylmethane series (VI) (3) is also known per se and may be performed by any prior art method. Suitable processes are described, for example, in EP 2 077 150 B1, EP 1 616 857 A1, EP 1 873 142 A1, and EP 0 314 985 B1.

The conversion of the aniline obtained by decarboxylating the aminobenzoic acid obtained in accordance with the invention to azo compounds, preferably to azo dyes (VI)(4) may be effected by any prior art method. Reference may be made by way of example to the known preparation of aniline yellow (para-aminoazobenzene; CAS 493-5-7) or indigo (2,2'-bis(2,3-dihydro-3-oxomethylidene); CAS 482-89-3) (Per Wiklund et al., *Current Organic Synthesis*, 2006, 3, 379-402).

The conversion of the aminobenzoic acid obtained in accordance with the invention to an amide (VI)(5) may be effected by any prior art method. Mention may be made by way of example of the primary amine of anthranilic acid (2-aminobenzylamide), which is used inter alia as starting material for the preparation of pharmaceuticals (Per Wiklund et al., *Current Organic Synthesis*, 2006, 3, 379-402).

The conversion of the aminobenzoic acid obtained in accordance with the invention to a conductive polymer such as preferably polyanthranilic acid (VI)(6) may be effected by any prior art method. An example is described in Bhavana Guptaa et al., *Polymers Advanced Technologies,* 2011, 22, 1982-1988.

The process of the invention is notable for various advantages, such as preferably the following:

- Reduction in the concentration of dissolved aminobenzoic acid in the fermentation reactor and hence a reduction in the stress on the microorganisms (aminobenzoic acid in relatively high concentration is toxic to many microorganisms).
- The process of the invention advantageously enables inducement of crystallization of aminobenzoate in the form of aminobenzoic acid by injection of carbon dioxide. This makes it possible to dispense with the mineral acids customarily used, preferably hydrochloric acid, or to use these at most for isolation of residual amounts of aminobenzoate, such as preferably from the aqueous fermentation solution remaining in step (II)(1) after the isolation of the calcium aminobenzoate. Moreover, the filtrate remaining after removal of the crystallized aminobenzoic acid and expansion is recycled into the process (see also FIG. 1). Therefore, the procedure of the invention results not only in the saving of mineral acids but also in a considerable reduction in the salt burden of the wastewater.
- The inventive addition of a calcium salt in the fermentation in many cases enables a considerable saving of base in the fermentation (in "conventional" methods, sodium hydroxide solution is frequently added during the fermentation in order to avoid a drop in the pH of the fermentation broth).

The invention is elucidated in detail hereinafter by examples.

EXAMPLES

For reasons of linguistic simplification, reference is generally also made hereinafter to ortho-aminobenzoic acid even when it is present partly or entirely as the anion (aminobenzoate) owing to the prevailing pH. It is possible to depart from this when defined aminobenzoate compounds such as, in particular, precipitated calcium ortho-aminobenzoate or commercially available salts are being referred to.

Reagents Used:

oAB STOCK SOLUTION: Stock solution of ortho-aminobenzoic acid of concentration 500 g/L, prepared by dissolving sodium ortho-aminobenzoate in water at pH 7.0.

AMMONIUM STOCK SOLUTION 1: Stock solution of ammonium carbonate of concentration 105 g/L.

AMMONIUM STOCK SOLUTION 2: Stock solution of ammonium carbonate of concentration 210 g/L.

FERMENTATION BROTH: Prepared by fermentation of an ortho-aminobenzoic acid-producing bacterium as described in WO 2015/124687 A1 on p. 35 and p. 36 in the "General cultivation of *Corynebacterium glutamicum* ATCC13032 based strains" section; contains ortho-aminobenzoic acid in a concentration of 13.0 g/L.

PRECULTURE MEDIUM I: The medium contains the following components dissolved in demineralized water: 16 g/L soya peptone, (Duchefa, Lot. No. 021679.01), 10 g/L yeast extract (Gistex LS FERM Batch, AFG2D10), 5 g/L NaCl and 15 g/L glucose (autoclaved separately).

PRECULTURE MEDIUM II: The medium contains the following components dissolved in demineralized water: 40 g/L glucose (autoclaved separately), 20 g/L $(NH_4)_2SO_4$, 5 g/L urea, 42 g/L MOPS buffer, 5 g/L yeast extract (Gistex LS FERM Batch AFG2D10), 1 g/L $KH_2PO_4$, 1 g/L $K_2HPO_4$, 0.25 g/L $MgSO_4.7 H_2O$, 0.01 g/L $CaCl_2$, 2 mg/L biotin (addition of 1 mL/L of a biotin stock solution having 2 g/L biotin, sterilized by 0.2 µm filtration) and 1 mL of the trace element stock solution (sterilized by 0.2 µm filtration)

GROWTH MEDIUM: The medium contains the following components dissolved in demineralized water: 20 g/L glucose (autoclaved separately), 5 g/L $(NH_4)_2SO_4$, 4 g/L $KH_2PO_4$, 4 g/L $K_2HPO_4$, 2 g/L $MgSO_4.7 H_2O$, 0.04 g/L $CaCl_2.2 H_2O$, 5 g/L yeast extract (Gistex LS FERM Batch: AFG2D10), 5 g/L polypropylene glycol 2000 (antifoam), 2 mg/L biotin (addition of 1 mL/L of a biotin stock solution having 2 g/L biotin, sterilized by 0.2 µm filtration) and 10 mL of the trace element stock solution (sterilized by 0.2 µm filtration)

MAIN CULTURE MEDIUM I: The medium contains the following components dissolved in demineralized water: 40 g/L glucose (autoclaved separately), 3.6 g/L $(NH_4)_2CO_3$, 4 g/L $KH_2PO_4$, 4 g/L $K_2HPO_4$, 2 g/L $MgSO_4.7 H_2O$, 0.04 g/L $CaCl_2.2 H_2O$, 1 g/L polypropylene glycol 2000 (antifoam), 2 mg/L biotin (addition of 1 mL/L of a biotin stock solution having 2 g/L biotin, sterilized by 0.2 µm filtration) and 10 mL of the trace element stock solution (sterilized by 0.2 µm filtration)

MAIN CULTURE MEDIUM II: The medium contains the following components dissolved in demineralized water: 40 g/L glucose (autoclaved separately), 10 g/L $(NH_4)_2CO_3$, 3.2 g/L $K_2CO_3$, 2.25 g/L $K_2HPO_4$, 2 g/L $MgSO_4.7 H_2O$, 20 g/L $CaCO_3$, 1 g/L polypropylene glycol 2000 (antifoam), 2 mg/L biotin (addition of 1 mL/L of a biotin stock solution having 2 g/L biotin, sterilized by 0.2 µm filtration) and 10 mL of the trace element stock solution (sterilized by 0.2 µm filtration)

TRACE ELEMENT STOCK SOLUTION: Aqueous solution having 10 g/L $MnSO_4.H_2O$, 10 g/L $FeSO_4.7 H_2O$, 1 g/L $ZnSO_4.7 H_2O$, 0.2 g/L $CuSO_4.5 H_2O$, 0.02 g/L $NiCl_2.6 H_2O$. The components are dissolved by addition of HCl at pH 1.

GLUCOSE-TRYPTOPHAN STOCK SOLUTION: Aqueous solution having 480 g/L glucose and 1.6 g/L tryptophan.

GLUCOSE STOCK SOLUTION: 600 g/L glucose solution, sterilized by autoclaving.

AMMONIA BASE: Aqueous ammonia solution of a concentration, calculated as $NH_3$, of 4.5 mol/L.

Example 1: Proof-of-Principle Experiment for Formation of Insoluble Calcium Ortho-Aminobenzoate in a Fermentation Broth and Dissolution Thereof by Salt Exchange with Ammonium Ions 48.0 g of anhydrous calcium chloride was added to 1.00 L of fermentation broth. The pH was adjusted to a value of 7.0 by adding hydrochloric acid. 100 g of ortho-aminobenzoic acid (dissolved in sodium hydroxide solution at pH 7.0) was then added to this mixture by adding 200 mL of oAB STOCK SOLUTION. There was briefly precipitation of calcium ortho-aminobenzoate. The concentration of dissolved ortho-aminobenzoic acid measured in the aqueous phase was 18.0 g/L. The solids fraction of the mixture was filtered off and dried at 80° C. for 48 h. In this way, 110 g of dried solid material was obtained. 20.0 g of that was added to 50.0 mL of AMMONIUM STOCK SOLUTION 1, the mixture was stirred and the concentration of dissolved ortho-aminobenzoic acid was determined. The latter was 146 g/L.

Example 2: Proof-of-Principle Experiment for Formation of Insoluble Calcium Ortho-Aminobenzoate in Water and Dissolution Thereof by Salt Exchange with Ammonium Ions 48.0 g of anhydrous calcium chloride was added to 800 mL of water. The pH was adjusted to a value of 7.0 by adding hydrochloric acid. 100 g of ortho-aminobenzoic acid (dissolved in sodium hydroxide solution at pH 7.0) was then added to this mixture by adding 200 mL of oAB STOCK SOLUTION. There was briefly precipitation of calcium ortho-aminobenzoate. The concentration of dissolved ortho-aminobenzoic acid measured in the aqueous phase was 18.0 g/L. The solids fraction of the mixture was filtered off and dried at 80° C. for 48 h. In this way, 110 g of dried solid material was obtained. 20.0 g of that was added to 25.0 mL of AMMONIUM STOCK SOLUTION 2, the mixture was stirred and the concentration of dissolved ortho-aminobenzoic acid was determined. The latter was 175 g/L.

Example 3: Proof-of-Principle Experiments for Determination of the Solubility of Calcium Ortho-Aminobenzoate in Water 3.00 g of dried calcium ortho-aminobenzoate was stirred into 100 mL of demineralized water and stirred at room temperature for 10 min. Subsequently, the concentration of dissolved ortho-aminobenzoic acid was determined in the aqueous phase. The latter was 17.0 g/L.

3.00 g of dried calcium ortho-aminobenzoate was stirred into 50 mL of demineralized water and stirred at room temperature for 10 min. Subsequently, the concentration of dissolved ortho-aminobenzoic acid was determined in the aqueous phase. The latter was 17.5 g/L.

Examples 4 and 5: Fed-Batch Fermentation of an Ortho-Aminobenzoate-Producing *C. glutamicum* Strain with Inclusion of Calcium Carbonate in the Initial Charge Growth of a preculture of an ortho-aminobenzoate-producing *C. glutamicum* strain in 25 mL of PRECULTURE MEDIUM I. The culture was incubated in a 300 mL Erlenmeyer flask in a shaking incubator having a shaking diameter of 5 cm at 30° C. and 200 rpm for 6 hours.

Subsequently, 20 mL of the culture was divided between 2×50 mL of PRECULTURE MEDIUM II and incubated in a shaking incubator having a shaking diameter of 5 cm at 30° C. and 200 rpm for 5 hours.

On conclusion of the incubation time for the second preculture, 40 mL of the second preculture was transferred into the growth fermenter. The growth fermenter was initially charged with a starting volume of 0.76 L of GROWTH MEDIUM, with the amount of all media components except for glucose intended for a volume of 1.00 L. The amount of glucose added was chosen such that there was a concentration of 40 g/L in a volume of 0.80 L (volume initially charged including volume of the preculture). The growth fermenter was operated by fed-batch operation in the range from 5.0 to 50 g/L glucose by addition of GLUCOSE-TRYPTOPHAN STOCK SOLUTION at a culturing temperature of 30° C. The pH was kept constant in the course of cultivation by the addition of AMMONIA BASE. The fermenter was sparged with 0.2 L/min of air, while controlling the dissolved oxygen by adjusting the stirrer speed between 200 and 1200 rpm at 30% air saturation. The growth fermenter was operated in fed-batch operation for a cultivation time of 24 hours.

On conclusion of the incubation time for the growth fermenter, 50 mL of the culture was transferred into a main culture fermenter in order to establish a starting $OD_{600}=20$. Four main culture fermenters were inoculated, with two fermenters operated with MAIN CULTURE MEDIUM without $CaCO_3$ (example 4—comparison) and two fermenters with an additional 20 g/L $CaCO_3$ in the medium (example 5—inventive step (I)). The results without the addition of $CaCO_3$ are shown in FIG. 2. The results for the reactors in which $CaCO_3$ was additionally added are shown in FIG. 3. Each fermenter was initially charged with a starting volume of 0.55 L of MAIN CULTURE MEDIUM I, with the amount of all media components including $CaCO_3$, except for glucose, intended for a volume of 1.00 L. The amount of glucose added was chosen such that there was a concentration of 40 g/L in a volume of 0.60 L (volume initially charged including inoculum). The main culture fermenter was operated by fed-batch operation in the range from 5.0 to 50 g/L glucose by addition of GLUCOSE STOCK SOLUTION at a culturing temperature of 30° C. The pH was kept constant at pH=7.0 in the course of cultivation by the addition of AMMONIA BASE. The fermenter was sparged with 0.2 L/min of air, while controlling the dissolved oxygen by adjusting the stirrer speed between 200 and 1200 rpm at 30% air saturation. The main culture fermenter was operated in fed-batch operation for a cultivation time of 50 hours. The progression of dry biomass, amount of ortho-aminobenzoic acid (oAB) produced and glucose consumed in the course of fermentation, as shown in figures FIG. 2 and FIG. 3, shows that the addition of $CaCO_3$ in solid form has a positive effect on the amount of oAB produced and the amount of glucose converted. The dry weight shown in FIG. 3 includes the solid $CaCO_3$ and the dried biomass; therefore the starting value for dry weight is much higher compared to the reactors without solid $CaCO_3$ in FIG. 2.

Example 6: Fed-Batch Fermentation of an Ortho-Aminobenzoate-Producing *C. glutamicum* Strain with Inclusion of Calcium Carbonate in the Initial Charge Growth of a preculture of an ortho-aminobenzoate-producing *C. glutamicum* strain in 25 mL of PRECULTURE MEDIUM I. The culture was incubated in a 300 mL Erlenmeyer flask in a shaking incubator having a shaking diameter of 5 cm at 30° C. and 200 rpm for 6 hours.

Subsequently, 20 mL of the culture was divided between 2×50 mL of PRECULTURE MEDIUM II and incubated in a shaking incubator having a shaking diameter of 5 cm at 30° C. and 200 rpm for 5 hours.

On conclusion of the incubation time for the second preculture, 50 mL of the second preculture was transferred directly into a main culture fermenter. Two main culture fermenters were operated. Each main culture fermenter was initially charged with a starting volume of 0.55 L of MAIN CULTURE MEDIUM II, with the amount of all media components except for glucose intended for a volume of 1.00 L. The amount of glucose added was chosen such that there was a concentration of 40 g/L in a volume of 0.60 L (volume initially charged including volume of the preculture). The main culture fermenters were operated by fed-batch operation in the range from 5.0 to 50 g/L glucose by addition of GLUCOSE STOCK SOLUTION at a culturing temperature of 30° C. The results of the fermentation are shown in FIG. 4 and FIG. 5. In order to reduce the starting pH to a value of below 8.6, the $CO_2$ content in the feed air was adjusted to 5% by volume in the first 15 hours of the fermentation. After a fermentation time of 15 hours, the sparging in both fermenters was switched to air and maintained for the further progression of the fermentation. The addition of AMMONIA BASE after 48 h prevented the pH from falling below a value of 6.8. Only after a fermentation time of 68 h was the addition of AMMONIA BASE stopped in order to further reduce the pH. The fermenters were sparged with a volume flow of 0.2 L/min of an oxygenous gas mixture, while controlling the dissolved oxygen by adjusting the stirrer speed between 200 and 1200 rpm at 30% air saturation. The progression of dry biomass, amount of ortho-aminobenzoic acid (oAB) produced and glucose consumed in the course of fermentation, as shown in FIG. 4, shows that the addition of $CaCO_3$ in solid form has a positive effect on the amount of oAB produced and the amount of glucose converted. The dry weight shown in FIG. 4 includes the solid $CaCO_3$ and the dried biomass; therefore the starting value for dry weight is much higher compared to the reactors without solid $CaCO_3$ in FIG. 2. The reduction in pH shown in FIG. 5 to a pH of 6.8 accelerates the dissolution of $CaCO_3$. The amount of base required compared to the reactors without solid $CaCO_3$ in FIG. 2 was reduced by about 50% through the buffering effect of $CaCO_3$.

Example 7: Model for Precipitation of Anthranilic Acid from an Aqueous Ammonium Anthranilate Solution (See FIG. 6)

The model was written in the AspenPlus process simulation tool. The main components considered are water, ortho-aminobenzoic acid, ammonia and $CO_2$. The underlying thermodynamic model takes account of the equilibrium reactions, for example the forming of dihydrogencarbonate, dissociation reactions and the forming of salts or solid anthranilic acid. The equilibrium constants and Henry constants come from existing databases. In the model, a simple flash calculation is conducted, in which the steam content is equated to 0. Parameters calculated thus include the pressure established, the pH and the proportion of anthranilic acid in solid form. As shown in FIG. 6, it is possible to show by the model that, with the aid of $CO_2$ under a pressure of 100 bar, it is possible to crystallize 65.8% of the anthranilic acid out of an aqueous ammonium ortho-anthranilate solution (proportion by mass $w_{oAB}=0.3$).

Example 8: Experiment for Precipitation of Ortho-Aminobenzoic Acid Out of an Aqueous $NH_4$ Ortho-Aminobenzoate Solution (See FIG. 7)

Aqueous equimolar $NH_4$ ortho-aminobenzoate solutions having concentrations of 10%, 20% and 30% by mass of ortho-aminobenzoic acid were put under pressure by injection of $CO_2$ in a temperature-controlled phase equilibrium cell such that the pH is reduced in the liquid phase by the carbonic acid that forms. The defined addition of $CO_2$ was effected by means of a temperature-controlled screw press. The pH shift resulted in precipitation of solid ortho-aminobenzoic acid. At multiple pressure levels of up to 60 bar, samples of the liquid phase were taken and analyzed in order to determine the concentration of ortho-aminobenzoic acid in the liquid phase. A mass balance was subsequently used to calculate the precipitated proportion of ortho-aminobenzoic acid. The results show that a significant proportion (more than 50% of the ortho-aminobenzoic acid present in the solution) can be crystallized out of the aqueous solution at a pressure of up to 60 bar.

Removing the liquid phase subsequently achieved a separation of the solids from the liquid phase. By this procedure, it was possible to isolate ortho-aminobenzoic acid in solid form. FIG. 7 shows the experimentally determined proportion of precipitated ortho-aminobenzoic acid as a function of the $CO_2$ pressure.

The invention claimed is:

1. A process for preparing aminobenzoic acid or an aminobenzoic acid conversion product, comprising:
 (I) fermenting a raw material comprising:
   a fermentable carbon-containing compound, and
   a nitrogen-containing compound,
   in a fermentation reactor using a microorganism and a calcium salt, wherein the microorganism contains a genetic modification to accumulate aminobenzoic acid in the fermentation reactor,
   so as to obtain a mixture suspended in an aqueous fermentation solution, the mixture comprising undissolved microorganisms and precipitated calcium aminobenzoate;
 (II) (1) isolating the
   (1)(i) precipitated calcium aminobenzoate or
   (1)(ii) mixture comprising undissolved microorganisms and precipitated calcium aminobenzoate
   obtained in step (I) from the aqueous fermentation solution,
  (2) converting the aminobenzoate bound in the calcium aminobenzoate to a water-soluble form to form a water-insoluble calcium salt other than calcium aminobenzoate by adding an aqueous phase containing cations that form water-soluble aminobenzoate salts and anions that form water-insoluble calcium salts to the isolated calcium aminobenzoate from (1)(i) or to the mixture comprising undissolved microorganisms and precipitated calcium aminobenzoate from (1)(ii),
   so as to obtain a suspension comprising
   (2)(i) the precipitated water-insoluble calcium salt or
   (2)(ii) a mixture comprising undissolved microorganisms and the water-insoluble calcium salt
   in an aqueous solution of aminobenzoate, and
  (3) separating the aqueous solution of aminobenzoate obtained in step (2) from the precipitated water-insoluble calcium salt from (2)(i) or from the mixture comprising undissolved microorganisms and the water-insoluble calcium salt from (2)(ii);
 (III) introducing carbon dioxide at a pressure of greater than or equal to 1.50 $bar_{(abs.)}$ into the aqueous solution of aminobenzoate separated off in step (II)(3) to separate aminobenzoic acid out, so as to form a suspension containing aminobenzoic acid in an aqueous solution;
 (IV) isolating the aminobenzoic acid separated out in step (III) by lowering the pressure with release of carbon dioxide to give a carbon dioxide-depleted aqueous solution that has been freed of aminobenzoic acid separated out;
 (V) using the aqueous solution obtained in step (IV) that has been depleted of carbon dioxide and freed of aminobenzoic acid separated out as a constituent of the aqueous phase added in step (II)(2); and (VI) optionally further converting the aminobenzoic acid separated off in step (IV) to an aminobenzoic acid conversion product, wherein step (VI) comprises:
(1) decarboxylating the aminobenzoic acid to give aniline;
(2) decarboxylating the aminobenzoic acid to give aniline, followed by acid-catalyzed reaction of the aniline with formaldehyde to form di- and polyamines of the diphenylmethane series;
(3) decarboxylating the aminobenzoic acid to give aniline, followed by acid-catalyzed reaction of the aniline with formaldehyde to form di- and polyamines of the diphenylmethane series, followed by reaction with phosgene to form di- and polyisocyanates of the diphenylmethane series;
(4) decarboxylating the aminobenzoic acid to give aniline, followed by conversion of the aniline to an azo compound;
(5) converting the aminobenzoic acid to an amide; or
(6) converting the aminobenzoic acid to a conductive polymer, the conductive polymer optionally comprising polyanthranilic acid.

2. The process as claimed in claim 1, in which the calcium salt used in step (I) is selected from calcium carbonate, calcium hydrogencarbonate, calcium hydroxide, calcium oxide and mixtures thereof.

3. The process as claimed in claim 1, in which the aqueous phase added in step (II)(2) comprises lithium, sodium, potassium and/or ammonium cations.

4. The process as claimed in claim 1, in which the fermentation in step (I) is performed batchwise in fermentation cycles.

5. The process as claimed in claim 4, in which, on conclusion of a fermentation cycle,
(A)
step (II)(1) is conducted by discharging the aqueous fermentation solution obtained in step (I) from the fermentation reactor while retaining the mixture comprising undissolved microorganisms and precipitated calcium aminobenzoate suspended therein;
step (II)(2) is conducted by introducing the aqueous phase into the fermentation reactor so as to obtain a suspension containing a mixture comprising undissolved microorganisms and the water-insoluble calcium salt in an aqueous solution of aminobenzoate in the fermentation reactor; and
step (II)(3) is conducted by discharging the aqueous solution of aminobenzoate obtained in step (II)(2) from the fermentation reactor, while retaining the mixture comprising undissolved microorganisms and the water-insoluble calcium salt and making it available for the next fermentation cycle; or
(B)
step (II)(1) is conducted by discharging the aqueous fermentation solution obtained in step (I) from the fermentation reactor together with the mixture comprising undissolved microorganisms and precipitated calcium aminobenzoate suspended therein and separating the mixture comprising undissolved microorganisms and precipitated calcium aminobenzoate from the aqueous fermentation solution outside the fermentation reactor and recycling it into the fermentation reactor;
step (II)(2) is conducted by introducing the aqueous phase into the fermentation reactor so as to obtain a suspension containing a mixture comprising undissolved microorganisms and the water-insoluble calcium salt in an aqueous solution of aminobenzoate in the fermentation reactor; and
step (II)(3) is conducted by discharging the aqueous solution of aminobenzoate obtained in step (II)(2) from the fermentation reactor, while retaining the mixture comprising undissolved microorganisms and the water-insoluble calcium salt and making it available for the next fermentation cycle; or
(C)
step (II)(1) is conducted by discharging the aqueous fermentation solution obtained in step (I) from the fermentation reactor together with the mixture comprising undissolved microorganisms and precipitated calcium aminobenzoate suspended therein and separating the mixture comprising undissolved microorganisms and precipitated calcium aminobenzoate from the aqueous fermentation solution outside the fermentation reactor and introducing it into a vessel other than the fermentation reactor;
step (II)(2) is conducted by introducing the aqueous phase into the vessel other than the fermentation reactor so as to obtain a suspension containing a mixture comprising undissolved microorganisms and the water-insoluble calcium salt in an aqueous solution of aminobenzoate in the vessel other than the fermentation reactor; and
after the separation of the aqueous solution of aminobenzoate obtained in step (II)(2) from the mixture comprising undissolved microorganisms and the water-insoluble calcium salt in step (II)(3), the mixture separated off is introduced back into the fermentation reactor in a step (II)(4) and made available for the next fermentation cycle.

6. The process as claimed in claim 5, in which steps (I) and (II) are repeated until the desired amount of aminobenzoic acid is obtained in step (IV) or the microorganisms used in step (I) have to be replaced.

7. The process as claimed in claim 1, in which the fermentation in step (I) is performed continuously.

8. The process as claimed in claim 7, in which
(A)
mixture suspended in the aqueous fermentation solution and comprising undissolved microorganisms and precipitated calcium aminobenzoate is discharged continuously from the fermentation reactor and
after discharging, step (II)(1) is conducted by separating the insoluble microorganisms and precipitated calcium aminobenzoate from one another and from the aqueous fermentation solution;
step (II)(2) is conducted by adding the aqueous phase to the calcium aminobenzoate thus separated off;
and wherein the insoluble microorganisms separated off in step (II)(1) are recycled partly to completely into the fermentation reactor;
or in which
(B)
precipitated calcium aminobenzoate suspended in the aqueous fermentation solution is discharged continuously from the fermentation reactor while retaining the undissolved microorganisms and
after discharging, step (II)(1) is conducted by separating precipitated calcium aminobenzoate from the aqueous fermentation solution;

step (II)(2) is conducted by adding the aqueous phase to the calcium aminobenzoate thus separated off;
or in which (C)

mixture suspended in the aqueous fermentation solution and comprising undissolved microorganisms and precipitated calcium aminobenzoate is discharged continuously from the fermentation reactor and after discharging, step (II)(1) is conducted by separating the mixture comprising undissolved microorganisms and precipitated calcium aminobenzoate from the aqueous fermentation solution;

step (II)(2) is conducted by adding the aqueous phase to the mixture thus separated off; and after the separation of the aqueous solution of aminobenzoate obtained in step (II)(2) from the mixture comprising undissolved microorganisms and the water-insoluble calcium salt in step (II)(3), the mixture separated off is introduced back into the fermentation reactor in a step (II)(4) and made available for the further continuous fermentation;

or in which (D)

mixture suspended in the aqueous fermentation solution and comprising undissolved microorganisms and precipitated calcium aminobenzoate is discharged continuously from the fermentation reactor and after discharging, step (II)(1) is conducted by separating the mixture comprising undissolved microorganisms and precipitated calcium aminobenzoate from the aqueous fermentation solution;

step (II)(2) is conducted by adding the aqueous phase to the mixture thus separated off; and after the separation of the aqueous solution of aminobenzoate obtained in step (II)(2) from the mixture comprising undissolved microorganisms and the water-insoluble calcium salt in step (II)(3), the mixture separated off is separated in a step (II)(4a) into the constituents of undissolved microorganisms and water-insoluble calcium salt, and, in a step (II)(4b), one of the constituents separated from one another is returned to the fermentation reactor and made available for the further continuous fermentation.

9. The process as claimed in claim 1, in which (A)

aminobenzoic acid is crystallized out of the aqueous fermentation solution obtained in step (II)(1) by adding acid until attainment of a pH in the range from 3.0 to <4.0 and the crystallized aminobenzoic acid is isolated, leaving an aminobenzoic acid-depleted mother liquor;
or in which (B)

the step (II)(1) obtained aqueous fermentation solution is recycled into the fermentation from step (I).

10. The process as claimed in claim 1, in which step (IV) comprises:

(1) separating the aminobenzoic acid separated out and the aqueous solution from step (III) at a pressure equal to or greater than the pressure in step (III), and (2) decompressing the aqueous solution separated off in step (1) to release carbon dioxide, giving a carbon dioxide-depleted aqueous solution.

11. The process as claimed in claim 1, in which the water-insoluble calcium salt from (2)(i) that has been separated off in step (II)(3) or the mixture comprising undissolved microorganisms and the water-insoluble calcium salt from (2)(ii) is recycled into step (I).

12. The process as claimed in claim 1, in which the carbon dioxide released in step (IV) is collected and used in step (III).

13. The process as claimed in claim 1, in which microorganisms of a type comprising *Escherichia coli, Pseudomonas putida, Corynebacterium glutamicum, Ashbya gossypii, Pichia pastoris, Hansenula polymorpha, Yarrowia lipolytica, Zygosaccharomyces bailii* or *Saccharomyces cerevisiae* are used in step (I).

14. The process as claimed in claim 1, in which step (I) is conducted at a pH of 4.0 or greater.

15. The process as claimed in claim 1, in which step (II)(2) is conducted at a pH of >7.0.

16. The process of claim 1, wherein the fermentable carbon-containing compound comprises starch hydrolyzate, sugarcane juice, sugarbeet juice, a hydrolyzate of a lignocellulose-containing raw material, or a mixture thereof.

17. The process of claim 1, wherein the nitrogen-containing compound comprises gaseous ammonia, aqueous ammonia, an ammonium salt, urea or a mixture thereof.

18. The process of claim 3, in which the aqueous phase added in step (II)(2) comprises ammonium cations, and carbonate and/or hydrogencarbonate anions.

19. The process of claim 1, wherein the genetic modification comprises a genetic modification to downregulate anthranilate phosphoribosyltransferase activity.

* * * * *